United States Patent [19]

Uyeo

[11] Patent Number: 4,960,879
[45] Date of Patent: Oct. 2, 1990

[54] PROCESS FOR CARBAPENEM INTERMEDIATES

[75] Inventor: Shoichiro Uyeo, Kyoto, Japan

[73] Assignee: Shionogi & Co., Ltd., Osaka, Japan

[21] Appl. No.: 318,717

[22] Filed: Mar. 3, 1989

[30] Foreign Application Priority Data

Mar. 23, 1988 [JP] Japan .................................. 63-70763

[51] Int. Cl.$^5$ .......................................... C07D 205/08
[52] U.S. Cl. ...................................... 540/200; 540/302
[58] Field of Search ............................... 540/200, 357

[56] References Cited

FOREIGN PATENT DOCUMENTS 35689 9/1981 European Pat. Off. ............ 540/200

OTHER PUBLICATIONS

March, Advanced Organic Chemistry, pp. 405–407.

Primary Examiner—Robert Gerstl
Attorney, Agent, or Firm—Wenderoth, Lind & Ponack

[57] ABSTRACT

A novel intermediate for synthesizing 1 β-alkyl-1-carbapenem, i.e., 4 β-(1 β-alkyl-2-carboxyprop-2-enyl)azetidin-2-one (II), is prepared stereoselectively by treating 4-(leaving group substituted)azetidin-2-one (I) with trans-2-(leaving group substituted)-methyl-3-alkylacrylic acid (III) and a reducing metal.

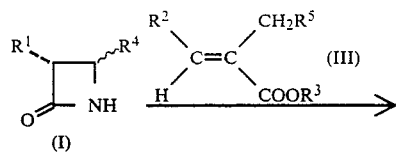

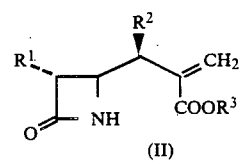

wherein
$R^1$ is hydrogen, alkyl, or substituted alkyl;
$R^2$ is optionally substituted alkyl;
$R^3$ is hydrogen or a carboxy-protecting group; and
$R^4$ and $R^5$ each is a leaving group.

17 Claims, No Drawings

PROCESS FOR CARBAPENEM INTERMEDIATES

This invention relates to an intermediate for preparing 1β-alkyl-1-carbapen-2-ems and its efficient synthesis. More specifically, it provides a method for preparing 4β-(1β-alkyl-2-carboxyprop-2-enyl)azetidin-2-one (II) by treating 4-(leaving group substituted azetidin-2-one (I) with 2-(leaving group substituted)methyl-3-alkylacrylic acid (III) and a reducing metal. It also provides the product, i.e., 4β-(1β-alkyl-2-carboxyprop-2-enyl)azetidin-2-one (II).

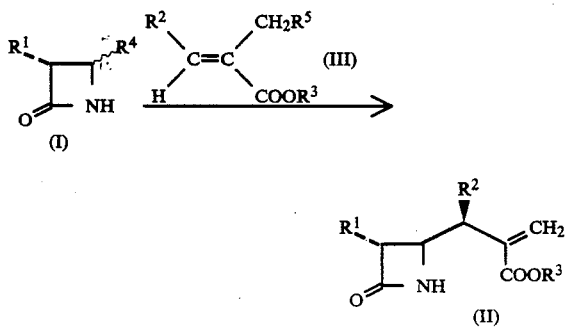

wherein,
$R^1$ is hydrogen or optionally substituted alkyl;
$R^2$ is optionally substituted alkyl;
$R^3$ is hydrogen or a carboxy-protecting group; and
$R^4$ and $R^5$ each is a leaving group.

[USE]

The produced 4β-(1β-alkyl-2-carboxyprop-2-enyl)azetidin-2-one (II) is useful as a starting material for producing, for example, a known or new antibacterial 6α-(1-hydroxyethyl)-1β-alkyl-2-heterocyclylthiomethyl-1-carbapen-2-em-3-carboxylic acid (b) through 1β-alkyl-2-hydroxymethyl-1-carbapen-2-em (a) in a manner as given under the section entitled [Additional Reactions] set forth below by way of novel or analogous reaction processes.

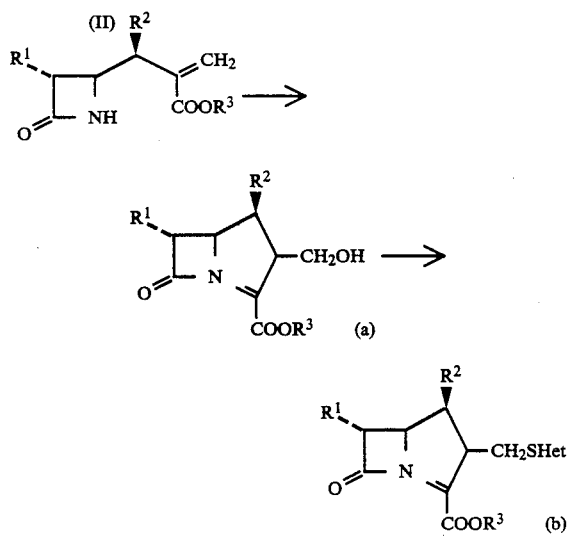

In 4β-(1β-alkyl-2-carboxyprop-2-enyl)azetidin-2-one (II) and its derivatives, β-lactam compounds (1) through (7), (a), (b) as disclosed in this specification, the position 3 and 4 on the azetidinone ring have stereochemistry the same as that of thienamycin, i.e., 3α-carbon, 3β-hydrogen, 4α-hydrogen, 4β-carbon. The 1-$R^2$ group in the side chain as introduced by the method of this invention has the stereochemistry which results in the β-isomer after cyclization.

The terms cis and trans showing the geometric isomers of the acrylic acid derivative (III) show relative position of the $R^2$ and $COOR^3$ groups. In the intermediate azetidinones (I), (II), (1) thorough (7), (a), and (b) as given below, the expression α and β showing stereochemistry of the groups attaching to the azetidinone ring corresponds to the groups in 1-carbapen-2-ems (a) and (b) derived from each intermediates. When $R^1$ is 1-acetoxyethyl, its absolute configuration is determined to be R.

[TECHNICAL FIELD OF THIS INVENTION]

The final objective 1β-alkyl-1-carbapen-2-ems (e.g., (b) see below) derivable from the objective compounds (II) of this invention are superior antibacterials useful for preventing or treating human or veterinary infections.

[LITERATURES]

The following references are representative literatures for synthesizing 1β-alkyl-1-carbapen-2-ems.

(1) Producing α,β-isomers mixture and then resolving them: Tetrahedron Letters, 26, 583 (1985), Jpn. Patent Appln. Kokai No. 60-158167, etc.;

(2) Methylating 1-carbanion and inversing the produced 1α-methyl group: Heterocycles, 21, 29 (1984), etc.;

(3) Forming a carbon to carbon bond on a 4-leaving group substituted azetidin-2-one: Aldrichimica Acta, 18, 95 (1985), Bull. Chem. Soc. Jpn., 59, 1363 (1986), J. Org. Chem., 50, 3438 (1985); Chemistry Lett., 1985, 1343; Tetrahedron Lett., 26, 4739 (1985), ibid., 28, 507 (1987), etc.;

(4) Forming a carbon to carbon bond by Aldol condensation: J. Am. Chem. Soc., 108, 4675 (1986), ibid., 108, 4673 (1986), Chem. Comm., 1986, 602, Tetrahedron Lett., 27, 5687 (1986), etc.;

(5) Orienting 1-methyl on 1-carbapen-2-em ring to β by reduction: Tetrahedron Lett., 28, 507 (1987), ibid., 27, 2149 (1987), ibid., 28, 1857 (1987), J. Org. Chem., 52, 2563 (1987), etc.; and (6) Deriving 1β-methyl from asymmetric sources: Tetrahedron Letters, 27, 247 (1986), ibid., 27, 6241 (1986), Jpn. Patent Appln. Kokai No. 62-29577, etc.

[THE PROBLEMS TO BE SOLVED BY THIS INVENTION]

The final objective 1β-alkyl-1-carbapenems preparable through this invention are superior antibacterials. However, the prior arts methods require many steps, low yield, an industrially unsuitable method for separating isomers, e.g., fractional recrystallization, fractional chromatography, at each steps for obtaining sterically pure products. Therefore, it was desirable to find out an economical and industrially feasible method based on a stereospecific reaction.

[THE EFFECT OF THIS INVENTION]

Now, the inventor found the following reaction for synthesizing intermediates (II) for producing the objective 1β-alkyl-1-carbapen-2-em compounds by reacting the sterically pure industrial starting material (I) and economically preparable reagent (III) under a mild condition. This reaction is stereoselective. The steric purity of the reaction product is high enough to obtain a product of high stereochemical purity easily only by simple crystallization. Thus, the problem of complicated and uneconomical handling of the known synthesis was solved.

As a result of the success in this particular step and the application of sterically uniformly proceeding succeeding steps, the final products, e.g., intermediate 1β-(1-substituted alkyl)-2-hydroxymethyl-1-carbapen-2-em (a) and antibacterially useful 6α-(1-hydroxyethyl)-1β-alkyl-2-heterocyclylthiomethyl-1-carbapen-2-em-3-carboxylic acid (b), can be industriallized efficiently by simple operations in high yield.

[THE METHOD FOR SOLVING THE PROBLEM]

According to this invention, 4-(leaving group substituted)-2-azetidinone (I) is treated with a trans-2-(leaving group substituted)methyl-3-alkylacrylic acid (III) and a reducing metal to produce 4β-(1β-alkyl-2-carboxyprop-2-enyl)azetidin-2-one (II).

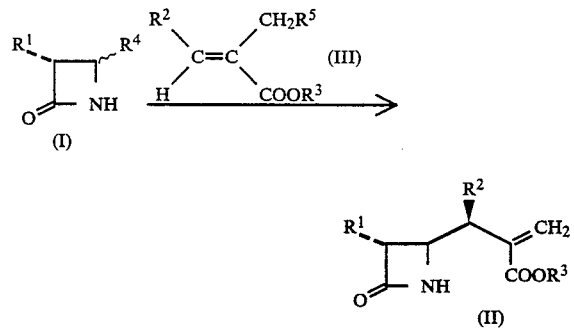

wherein,
$R^1$ is hydrogen or optionally substituted alkyl;
$R^2$ is optionally substituted alkyl;
$R^3$ is hydrogen or a carboxy-protecting group; and
$R^4$ and $R^5$ each is a leaving group.

[THE SYMBOLS]

In the above defined symbols, the $R^1$ group is a 6-substituent of penem or 1-carbapenem compounds. Preferable are hydrogen, 1C to 10C alkyl, or 1C to 10C 1-(hydroxy or halo)alkyl. The hydroxy in $R^1$ may be protected with a group which may be removed in a later step up to the finally objective compound.

Representative are 1C to 8C alkyl (e.g., methyl, ethyl, propyl), 1C to 8C hydroxyalkyl (e.g., hydroxymethyl, 1-hydroxyethyl, 1-hydroxypropyl, 2-hydroxyisopropyl), 1C to 8C haloalkyl (e.g., fluoromethyl, chloromethyl, 1-fluoroethyl, 2-fluoroisopropyl, trifluoromethyl), 4C to 8C dioxolenyl [for example, 2-oxo-4-(alkyl, e.g., methyl, ethyl, propyl)dioxolenyl], and the like. The hydroxy in hydroxyalkyl may be protected by, e.g., $R^6$ as given below.

$R^2$ is optionally substituted alkyl. Preferable is 1C to 8C alkyl. Representative are 1C to 3C alkyl (e.g., methyl, ethyl, propyl), 1C to 5C haloalkyl (e.g., fluoroalkyl, chloroalkyl, bromoalkyl), 1C to 5C carbon substituted alkyl (e.g., cyanoalkyl, carbamoylalkyl, carboxyalkyl, protected carboxyalkyl, alkenyl, alkinyl), 1C to 5C nitrogen substituted alkyl (e.g., aminoalkyl, ureidoalkyl, formimidoylalkyl), 1C to 5C oxygen substituted alkyl (e.g., hydroxyalkyl, alkanoyloxyalkyl, carbamoyloxyalkyl, hydroxyalkyloxyalkyl, aminoalkoxyalkyl, haloalkoxyalkyl), and 1C to 5C sulfur substituted alkyl (e.g., alkylthioalkyl, aminoalkylthioalkyl, hydroxyalkylthioalkyl, haloalkylthioalkyl, alkylsulfinylalkyl, aminoalkylsulfinylalkyl, hydroxyalkylsulfinylalkyl, haloalkylsulfinylalkyl, alkylsulfonylalkyl, aminoalkylsulfonylalkyl, hydroxyalkylsulfonylalkyl, haloalkylsulfonylalkyl), and the like. The $R^2$ having hydroxy may be protected as said in the section for $R^1$.

The group $R^3$ in formulas (II) and (III) is a hydrogen atom or a carboxy protective group. The latter is removed during the alanate reduction. So, structurally simple esters (e.g., 1C to 8C alkyl ester) are preferable, although non-simple ones can be chosen.

The group $R^7$ in the formulas (4) to (b) as given below may be a hydrogen atom or a carboxy protective group. The protective group may have 1 to 19 carbon atoms and can be removed without adverse effect on the other part of the molecule well known in the field of beta-lactam chemistry.

The representative carboxy protective groups $R^3$ and $R^7$ are, for example, 1C to 8C alkyl (e.g., methyl, methoxymethyl, ethyl, ethoxymethyl, iodoethyl, propyl, isopropyl, butyl, isobutyl, ethoxyethyl, methylthioethyl, methanesulfonylethyl, trichloroethyl, tert.-butyl), 3C to 8C alkenyl (e.g., propenyl, allyl, prenyl, hexenyl, phenylpropenyl, dimethylhexenyl), 7C to 19C aralkyl (e.g. benzyl, methylbenzyl, dimethylbenzyl, methoxybenzyl, ethoxybenzyl, nitrobenzyl, aminobenzyl, diphenylmethyl, phenylethyl, trityl, di-t-butylhydroxybenzyl, phthalidyl, phenacyl), 6C to 12C aryl (e.g., phenyl, tolyl, diisopropylphenyl, xylyl, trichlorophenyl, pentachlorophenyl, indanyl), 1C to 12C amino (a group for forming an ester with e.g., acetone oxime, acetophenone oxime, acetaldoxime, N-hydroxysuccinimide, N-hydroxypthalimide), 3C to 12C alkylsilyl (e.g., trimethylsilyl, dimethylmethoxysilyl, tert.-butyldimethylsilyl), 3C to 12C alkylstannyl (e.g., trimethylstannyl), and the like. This carboxy protective group is eliminated on the way up to final objective compounds, the structure has no important meaning so far as the protection can be effected. A wide variety of equivalent groups (e.g., amide, carbonic or carboxylic acid anhydride) are available for the same purpose. Representative salt forming carboxy protective atoms or groups $R^7$ include that well known in the field of beta-lactam chemistry, e.g., a light metal of group I to III, period 2 to 4 of the periodical table, i.e., lithium, sodium, potassium, magnesium, calcium, aluminum, etc., and ammonium for synthetic purposes, for example, 1C to 12C alkylammonium (e.g., trimethylammmonium, triethylammonium, methylmorpholinium), 4C to 9C arylium (e.g., pyridinium, collidinium, picolinium, quinolinium, dimethylanilinium), and the like.

$R^4$ and $R^5$ each is a leaving group. Representative are hydroxy, acyloxy {for example, carboxylic acid acyloxy (e.g., 1C to 8C optionally substituted alkanoyloxy, 7C to 15C aroyloxy), sulfonic acyloxy (e.g., 1C to 8C optionally substituted alkylsulfonyloxy, 6C to 10C arylsulfonyloxy), and the like}, sulfinyl (e.g., 1C to 8C alkylsulfinyl, 6C to 10C arylsulfinyl), halogen (e.g., fluorine, chlorine, bromine), and the like.

$R^6$ in formulas (2) to (b) as given below is hydrogen or a hydroxy protective group.

Representative hydroxy protective groups are well known removable ester forming group [for example, 1C to 10C carboxylic acyl (e.g., 1C to 8C alkanoyl or aroyl), 2C to 10C carbonic acyl (e.g., lower alkoxycarbonyl, chloroalkoxycarbonyl, benzyloxycarbonyl, p-nitrobenzyloxycarbonyl, p-methoxybenzyloxycarbonyl, o-nitrobenzyloxycarbonyl, allyloxycarbonyl)], 2C to 8C ether forming group (e.g., methoxymethyl, methoxyethoxymethyl, tetrahydrofuranyl, tetrahydropyranyl), 3C to 18C hydrocarbylsilyl (e.g., trimethylsilyl, triethylsilyl, dimethylphenylsilyl, diphenylmethylsilyl, diphenyl-tert.-butylsilyl, dimethyl-tert.-pentylsilyl), 7C to 19C active aralkyl (e.g., triphenylmethyl), and the like.

Het in formulas (7) and (b) is a heterocyclic aryl group.

The said $R^1$ to $R^7$ and Het are optionally substituted further to those specifically disclosed above. The said carbon numbers for $R^1$ to $R^7$ are to include that of protective group. A group reactive under the reaction condition to result in an adverse change may be preferably protected prior to the reaction and then deprotected later.

In the said groups, the alkyl part is straight, branched, cyclic, or partly cyclic alkyl optionally substituted or unsaturated. Representative alkyl are methyl, ethyl, propyl, isopropyl, cyclopropyl, butyl, isobutyl, tert.-butyl, cyclobutyl, cyclopropylmethyl, pentyl, isopentyl, neopentyl, cyclopentyl, cyclobutylmethyl, hexyl, cyclohexyl, cyclopentylethyl, heptyl, cycloheptyl, cyclopentylethyl, cyclo-hexylmethyl, octyl, cyclooctyl, cyclohexylethyl, nonyl, dodecyl, and the like.

The aralkyl part is a combined alkyl part and aryl part. Representative aralkyl are optionally substituted benzyl, phenylethyl, phenylpropyl, phenylisopropyl, naphthylmethyl, furylmethyl, thienylpropyl, oxazolylmethyl, thiazolylmethyl, imidazolylmethyl, triazolylmethyl, pyridylmethyl, indolylmethyl, benzoimidazolylethyl, benzothiazolylmethyl, quinolylmethyl, and the like.

The acyl part is optionally substituted straight, branched or cyclic alkanoyl, alkylsulfonyl, carbamoyl, carbalkoxy, sulfo, or the like, or alternatively it is monocyclic or dicyclic, carbocyclic or heterocyclic optionally substituted aroyl, aralkanoyl, arylalkenoyl, arylsulfonyl, carboaralkoxy, or the like.

The aryl part is optionally substituted by 5 to 6 membered monocyclic or dicyclic and carbocyclic or oxygen, nitrogen, and/or sulfur heterocyclic aryl. Representative are phenyl, naphthyl, indenyl, furyl, thienyl, pyrrolyl, oxazolyl, thiazolyl, imidazolyl, oxadiazolyl, thiadiazolyl, triazolyl, thiatriazolyl, tetrazolyl, pyridyl, pyranyl, indolyl, benzofuyl, benzothienyl, benzoimidazolyl, benzothiazolyl, benzopyrazinyl, quinolyl, pyridopyridyl, and the like.

The halogen is fluorine, chlorine, bromine, or iodine, or alternatively equivalent pseudohalogen (e.g., alkanesulfonyloxy, arylsulfonyloxy, trifluoromethanesulfonyloxy, trifluoroacetoxy, cyano, thiocyanato, isothiocyanato).

The representative substituents to be bond to said groups are a carbon function (e.g., straight, branched, or cyclic alkyl, alkenyl, alkinyl, aralkyl, aryl, heterocyclic group, carboxylic acyl, carbamoyl, carboxy, protected carboxy, cyano); a nitrogen function (e.g., amino, acylamino, guanidinyl, ureido, alkylamino, dialkylamino, isothiocyano, isocyano, nitro, nitroso), an oxygen function (e.g., hydroxy, alkoxy, aryloxy, heterocyclyloxy, cyanato, oxo, carboxylic acyloxy, sulfonic acyloxy, phosphoric acyloxy), a sulfur function (e.g., mercapto, alkylthio, alkylsulfonyl, arylthio, arylsulfonyl, heterocyclylthio, heterocyclylsulfonyl, acylthio, thioxo, sulfo, sulfamoyl), halogen (e.g. fluorine, chlorine, bromine, iodine), silyl (e.g., trialkylsilyl, dialkylalkoxysilyl), stannyl (e.g., trialkylstannyl), and the like.

[REACTION OF THIS INVENTION]

According to the process of this invention, 4-(leaving group substituted)azetidin-2-one compound (I) is treated with trans-2-(leaving group substituted)methyl-3-alkylacrylic acid compound (III) and a reducing metal to give 4β-(1β-alkyl-2-carboxyprop-2-enyl)azetidin-2-one compound (II) as follows:

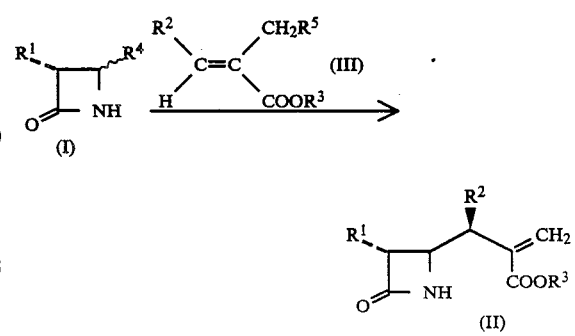

wherein,
$R^1$ is hydrogen or optionally substituted alkyl,
$R^2$ is optionally substituted alkyl,
$R^3$ is hydrogen or a carboxy protecting group, and
$R^4$ and $R^5$ each is a leaving group.

This reaction is usually carried out in a solvent. The solvent is an aliphatic hydrocarbon, aromatic hydrocarbon, halohydrocarbon, ether, ester, nitrile, amide, sulfoxide, aromatic base, alcohol, or the like inert and the starting materials dissolving solvent or a mixture of these. More preferable are amide and etheric solvents.

The reaction is carried out at −10° to 50° C., preferably at around room temperature. Under this condition, the reaction usually completes within 0.5 to 10 hours. The reaction mixture may be stirred, dried (e.g., with molecular sieve), or sealed with an inert gas. The crude yield of the product with high steric purity amounts up to 85 to 99%.

[OTHER STARTING MATERIALS]

The trans-2-(leaving group substituted)methyl-3-alkylacrylate (III) is prepared in high yield, for example, by condensing acrylate ester (IV) with alkanal (V) in the presence of a tertiary base (e.g., trialkylamine, 4-methylmorpholine, quinuclidine, dimethyl-aniline) to produce 2-(1-hydroxyalkyl)acrylate (VI) and this is subjected to a halogen substitution (e.g., with hydrogen halide) at around room temperature under a dehydrating condition (e.g., with concentrated sulfuric acid).

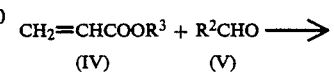

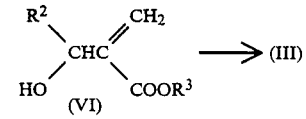

The representative reducing metal for this invention is that having the oxido-reduction potential of −0.1 to −0.8 volt {to a hydrogen electrode (e.g., zinc, chrome, galium, iron, cadmiun, indium, thalium, cobalt, nickel, molybden, tin) including its salts}. The metal can conventionally be activated by treating with a heavy metal salt, for example, a copper salt (e.g., cupric chloride, cuprous bromide) or a mercury salt (e.g., mercuric chloride, mercury acetate), or with an acid {for example, a mineral acid (e.g., hydrochloric acid, sulfuric acid, hydrobromic acid), a strong carboxylic acid, or the like}.

[EFFECT OF THIS INVENTION]

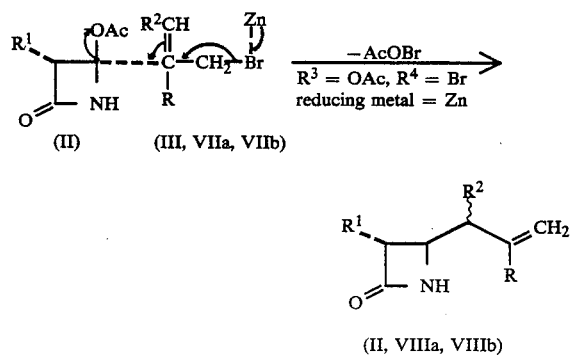

TABLE I

| Reagent | Yield | 1 β-isomer |
|---|---|---|
| (This invention: carboxylate) | | |
| methyl ester (III) | 96% | >95% |
| ethyl ester (III) | 80% | >95% |
| (Reference: protected methylol) | | |
| trityl ether (VII a) | 34% | ca.50% |
| acetate (VII b) | 13% | ca.71% |

This invention is new reductive substitution. The carboxy of reagent (III) is a requisite for stereoselective reaction. This is proven by comparing a reaction of reactant (I) and reagent (III: R=COO-alkyl) giving purer 1β-$R^2$ isomer (II: R=COO-alkyl) according to this invention with that of reactant (I) and methylol tritylate (VII: R=CH$_2$O-trityl) or methylol acetate (VIIa: R=CH$_2$O-acetyl) giving a mixture of 1α- and 1β-$R^2$ isomers at the 4β-side chain (VIIIa: R=CH$_2$O-acetyl) and (VIIIb: R=CH$_2$O-trityl) in a lower yield under the same condition. For example, see Table I on page 14.

[USE OF THIS INVENTION]

The compound (II) preparable by this invention is useful as a starting material for producing 1β-alkyl-1-carbapen-2-ems (a). This compound (a) may further be subjected to a nucleophilic substitution (e.g., with heterocyclylthiol) and deprotection to produce a potent antibacterial finally objective 6α-(1-hydroxyethyl)-1β-alkyl-2-heterocyclylthiomethyl-1-carbapen-2-em-3-carboxylic acid or the like (b). Further reactions may lead the product (a) or (b) to other more potent antibacterial compound.

[AN ILLUSTRATED USE]

On the next page, reaction schema are given to illustrate some examples of how to use the product of this invention (II). For example, 1β-alkyl-2-hydroxymethyl-1-carbapen-2-em (a) can be produced in high yield from compound (II) by a combination of some of the additional reactions A to H as disclosed below.

In the schema, $R^1$, $R^2$, $R^3$, and $R^6$ are as given above; $R^7$ is hydrogen, a negative charge or a carboxy protective group; Ar is aryl; and Het is a heterocyclic aryl group.

[ADDITIONAL REACTIONS]

The following succeeding steps A to H are known as unit processes. Thus, the reaction conditions (e.g., solvent, reagent, temperature, time) suitable for each starting material can be selected from known literatures.

The compounds (1) through (6) are novel compounds. Therefore, each steps are novel analogous reactions.

A: Reduction of carboxy.
B: Protection and deprotection of hydroxy.
C: Fission of double bond.
D: Addition of glyoxylic acid.
E: Cyclization.
F: Nucleophylic substitution.
G: Carboxy deprotection.
H: Additional treatment.

The reaction conditions of A to H are illustrated below:

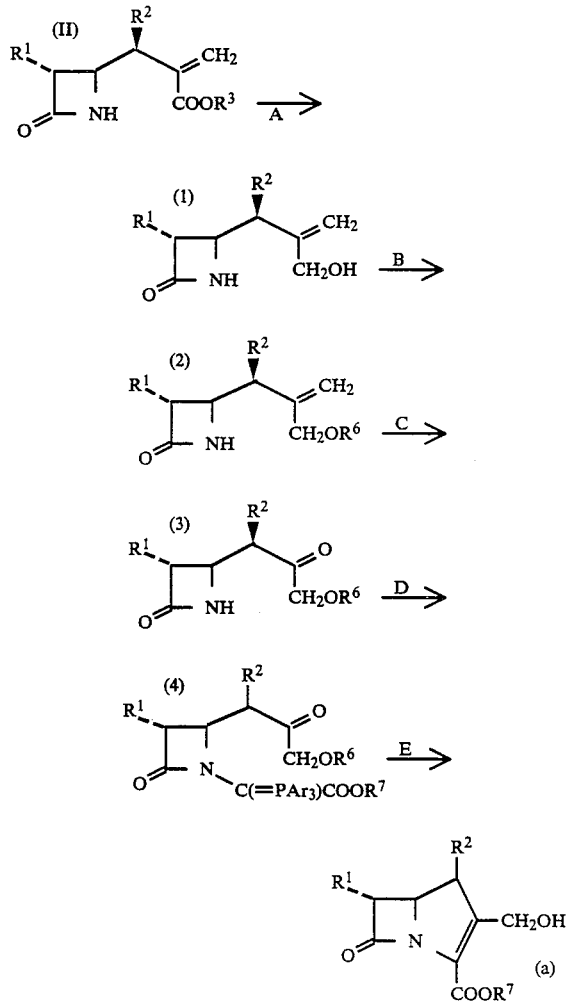

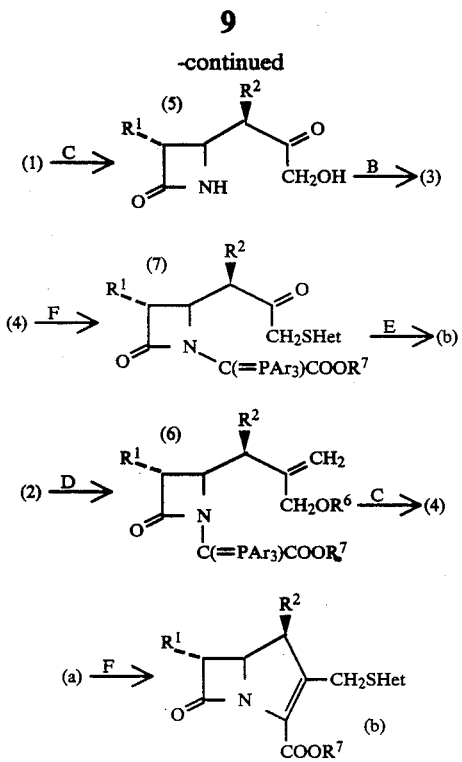

A: Reduction of carboxy

In a stirring inert solvent (e.g., toluene) at −10° to 30° C. the starting carboxylate ester is treated with an aluminum hydride reducing reagent (1 to 5 equivalents of e.g. diisobutylaluminum hydride) for 1 to 5 hours to give the corresponding primary alcohol.

B: Protection and deprotection of hydroxy (a) Acetate ester

In a stirring inert solvent (e.g., dichloromethane) at −10° to 30° C., the starting alcohol is treated with acetyl halide or acetic anhydride in the presence of a tertiary base (e.g., triethylamine) for 1 to 20 hours to give the corresponding acetate ester. The protective acetate group can be deprotected e.g., with sodium methoxide in methanol.

(b) Trityl ether

In a stirring inert solvent (e.g., dichloromethane) at −10° to 50° C., the starting alcohol is treated with a triphenylmethyl halide for 1 to 20 hours in the presence of a tertiary base (e.g. triethylamine) to give the corresponding trityl ether. The trityl ether protective group can be deprotected with, e.g., hydrochloric acid in e.g., acetonitrile, acetic acid, ethyl acetate.

(c) tert.-Butyldimethylsilyl ether

In a stirring inert solvent (e.g., dimethylformamide) at −10° to 50° C., the starting alcohol is treated with a base (e.g., imidazole) and tert.-butyldimethylsilyl halide for 1 to 20 hours to give the corresponding tert.-butyldimethylsilyl ether. The tert-butyldimethylsilyl protective group can be deprotected e.g., with hydrochloric acid in acetonitrile.

C: Fission of the double bond

In a stirring inert solvent (e.g., dichloromethane, methanol) at −80° to −50° C., the starting alkene is treated with ozone for 1 to 20 hours, if required in the presence of acid (e.g., trifluoroacetic acid). The reaction mixture is treated with a reducing reagent (e.g., dimethyl sulfide, zinc) and subjected to work up giving the corresponding ketone.

D: Addition of glyoxylic acid (a) Glyoxylate addition:

In a stirring inert solvent (e.g., tetrahydrofuran) at 0° to 50° C., the starting azetidinone is treated with a glyoxylate ester (1 to 2 equivalents) for 1 to 30 hours, if required, in the presence of a base (e.g., triethylamine), to give the corresponding glyoxylate adduct.

(b) Halogenation

In a stirring inert solvent (e.g., tetrahydrofuran) at −20° to 50° C., the starting alcohol is treated with a halogenating reagent (e.g., thionyl chloride) (1 to 2 equivalents) for 1 to 5 hours in the presence of a base (e.g., 2,6-lutidine) to give the corresponding chloride.

(c) Ylide formation

In a stirring inert solvent (e.g., tetrahydrofuran, dioxane) at 0° to 50° C., the starting chloride is treated with triarylphosphine (1 to 2 equivalents) for 1 to 30 hours in the presence of a base (e.g., 2,6-lutidine) and a reaction accelerator (e.g., sodium bromide) to give the corresponding ylide.

E: Wittig cyclization.

In an inert solvent (e.g., benzene), the starting ylide is heated at 50° to 120° C. for 1 to 5 hours to give 1β-alkyl-1-carbapen-2-em compound.

F: Nucleophylic substitution.

(a) Chloro or mesyloxy derivative.

In a stirring inert solvent (e.g., dichloromethane, acetonitrile) at −70° to 30° C., the starting alcohol is treated with a nucleophilic reagent (1 to 2 equivalents of e.g., diphenylchlorophosphate, triphenylphosphine+-carbon tetrachloride, methanesulfonyl chloride) in the presence of a base (e.g., dimethylaminopyridine, triethylamine) for 1 to 5 hours, and then the mixture is treated with trimethylsilyl chloride (1 to 5 equivalents) for 1 to 8 hours to give the corresponding chloride or mesylate.

(b) (2 or 4)-Pyridylthio derivative.

In a stirring inert solvent (e.g., dichloromethane, acetonitrile, dimethylformamide) at −10° to −50° C., the starting chloro or mesyloxy derivative is treated with (2 or 4-mercapto)pyridine (1 to 2 equivalents) in the presence of a base (e.g., triethylamine) and a reaction promoter (e.g., sodium iodide) for 1 to 5 hours to give the corresponding (2 or 4-pyridylthio) derivative.

(c) (2 or 3)-Pyridylthio derivative.

In a stirring inert solvent (e.g., dichloromethane) at 10° to −70° C., the starting alcohol is treated with di(2 or 3-pyridyl)disulfide (1 to 2 equivalents) in the presence of a phosphine (e.g., tri-n-butylphosphine) for 1 to 5 hours to give (2 or 3-pyridylthio) derivative.

G: Carboxy deprotection.

The methoxybenzyl ester protective group can be deprotected by treating in a stirring inert solvent (e.g. dichloromethane) at 10° to −70° C. with a Lewis acid (0.1 to 2 weights of e.g., aluminum chloride) in the presence of a carbonium ion scavenger (e.g., anisole, thiophenol) for 1 to 5 hours.

The allyl ester protective group can also be deprotected by treating in a stirring inert solvent under ice cooling with a catalytic amount of palladium tetrakistriphenylphosphine and sodium ethylhexanonate (ca. 1 equivalent) for 1 to 5 hours to give the corresponding salt.

[REACTION TIME AND TEMPERATURE]

The said syntheses each is usually carried out at −30° C. to 100° C., especially −20° C. to 50° C., for 10 minutes to 10 hours. Preferably, these are carried out under dry condition in a solvent. Other conventional techniques are applicable.

[REACTION SOLVENT]

The reaction solvent for the reaction of this invention and the additional reactions A to H can be a hydrocarbon (e.g., pentane, hexane, octane, benzene, toluene, xylene), halohydrocarbon (e.g., dichloromethane, chloroform, carbon tetrachloride, dichloroethane, trichloroethane, chlorobenzene), ether (e.g., diethyl ether, methyl isobutyl ether, dioxane, tetrahydrofuran), ketone (e.g., acetone, methyl ethyl ketone, cyclohexanone), ester (e.g., ethyl acetate, isobutyl acetate, methyl benzoate), nitrohydrocarbon (e.g., nitromethane, nitrobenzene), nitrile (e.g., acetonitrile, benzonitrile), amide (e.g., formamide, acetamide, dimethylformamide, dimethylacetamide, hexamethylphosphorotriamide), sulfoxide (e.g., dimethyl sulfoxide), carboxylic acid (e.g., formic acid, acetic acid, propionic acid), organic base (e.g., diethylamine, triethylamine, pyridine, picoline, collidine, quinoline), alcohol (e.g., methanol, ethanol, propanol, hexanol, octanol, benzyl alcohol), water, or the like industrial solvent or a mixture of these.

[WORK UP]

The objective reaction products can be recovered from the respective reaction mixture after removing contaminants (e.g., unreacted starting material, by-products, solvents) by a conventional method (e.g., extracting, evaporating, washing, concentrating, precipitating, filtrating, drying) and can be isolated by a usual work up (e.g., adsorbing, eluting, distilling, precipitating, separating, chromatographying, crystallizing).

[EXAMPLES]

[The reaction of this invention]

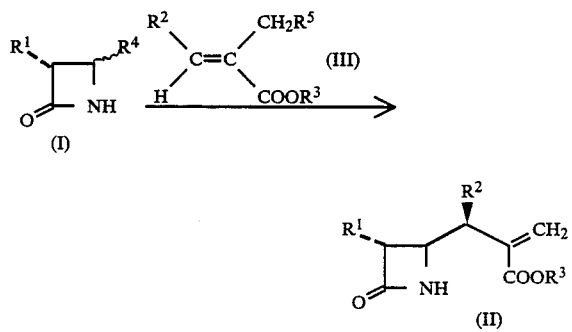

EXAMPLE I-1

$R^1$ = 1-(tert-butyldimethylsilyloxy)ethyl,
$R^2$ = methyl, $R^3$ = methyl, $R^4$ = acetoxy, $R^5$ = bromo.

Zinc powder (6.0 g) in tetrahydrofuran (80 ml) is stirred at room temperature in the presence of cupric bromide (150 mg) for 1 hour. To this mixture are added dropwise a solution of acetate (I) (14.35 g) in tetrahydrofuran (20 ml) and a solution of methyl 2-bromomethylbut-2-enoate (III) (12.0 g) in tetrahydrofuran (40 ml) at 30° to 35° C. during 2.5 hours. Then the mixture is stirred at the same temperature for 1 hour. The reaction mixture is diluted with ethyl acetate, stirred with saturated saline for 30 minutes, and filtered to remove solid using Celite. The organic layer is washed with saline, dried (MgSO₄), and concentrated to give crystalline residue (ca. 20 g). This is washed with n-hexane to give methyl ester of methyl derivative (II) (10.5 g). The washing is concentrated to dryness and purified by chromatography (toluene:ethyl acetate=9:1) over silica gel (110 g) to give further amount of compound (II) (5.88 g). Total: 16.38 g. mp. 100°–101.5° C. (from ether-n-hexane).

IR (Nujol)ν: 3155, 3088, 1752, 1717, 1622, 1251, 1140, 1050, 826 cm⁻¹.

NMR (VXR200, CDCl₃)δ: 0.06 (6H, s), 0.87 (9H, s), 1.14 (3H, d, J=6.2 Hz), 1.15 (3H, d, J=7.1 Hz), 2.84 (1H, m), 3.04 (1H, quintet, J=7.7 Hz), 3.74 (1H, dd, J=6 Hz, J=2.2 Hz), 3.76 (1H, s), 4.16 (1H, dq, J=6.2 Hz, J=4.4 Hz), 5.65 (1H, s), 5.91 (1H, brs), 6.32 (1H, d, J=0.8 Hz) ppm.

EXAMPLE I-2

$R^1$ = 1-(tert-butyldimethylsilyloxy)ethyl,
$R^2$ = methyl, $R^3$ = ethyl, $R^4$ = acetoxy, $R^5$ = bromo.

Under a condition similar to that of above methyl derivative methyl ester, the reaction of ethyl 2-bromomethylbut-2-enoate (III) with acetate (I) affords the objective ethyl ester of methyl derivative (II). Yield: 87.2%. mp 91.5°–92.5° C. (from hexane).

IR (CHCl₃)ν: 3380, 1750, 1700, 1611 cm⁻¹.

NMR (EM390, CDCl₃)δ: 0.83 (9H, s), 1.09 (3H, d, J=5 Hz), 1.10 (3H, d, J=6.3 Hz), 1.25 (3H, t, J=6.6 Hz), 2.82 (1H, m), 2.93, 3.13 (1H, m), 3.70 (1H, dd, J=6.0 Hz, J=2.0 Hz), 4.17 (2H, q, J=6.6 Hz), 4.0–4.28 (1H, m), 5.58 (1H, s), 6.15 (1H, brs), 6.27 (1H, s) ppm.

EXAMPLE I-3

$R^1$ = 1-(tert-butyldimethylsilyloxy)ethyl, $R^2$ = ethyl, $R^3$ = methyl, $R^4$ = acetoxy, $R^5$ = bromo.

Under a condition similar to that of above methyl ester or ethyl ester of methyl derivative, the reaction of acetate (I) (14.35 g) with methyl 2-bromomethylpent-2-enoate (III) in the presence of zinc and cupric bromide in tetrahydrofuran affords the objective methyl ester of ethyl derivative (II) (14.0 g). Yield: ca. 80%. mp 105.5°–106° C.

IR (Nujol)ν: 3150, 3100, 1760, 1727, 1626, 1256 cm⁻¹.

NMR (VXR200, CDCl₃)δ: 0.042 (ca. 6H, s), 0.86 (9H, s), 0.87 (3H, t, J=4.5 Hz), 1.09 (3H, d, J=6.3 Hz), 1.45–1.69 (2H, m), 2.71 (1H, m), 2.79 (1H, dd, J=2.9 Hz, J=1.1 Hz), 3.75–3.78 (1H, m), 3.75 (3H, s), 4.14 (1H, dq, J=6.3 Hz, J=2.9 Hz), 5.62 (1H, d, J=0.7 Hz), 5.89 (1H, brs), 6.38 (d, J=0.9 Hz) ppm.

EXAMPLE I-4

In a manner similar to those of above Examples I-1 to I-3, the following addition products (II) can be prepared.

| $R^1$ | $R^2$ | $R^3$ |
|---|---|---|
| CH₃ | CH₃ | CH₃ |
| CH₃ | C₂H₅ | CH₃ |
| FCH₂ | CH₃ | CH₃ |
| CH₃COOCH₂ | CH₂Cl | C₂H₅ |
| CH₃COOCH₂ | CH₂CN | C₄H₉ |
| (CH₃)₃CSi(CH₃)₂OCH₂ | CH₂F | CH₃ |
| C₂H₅ | CH₃ | CH₃ |
| C₂H₅ | CH₃ | C₂H₅ |
| C₂H₅ | CH₃ | C₃H₇ |
| C₂H₅ | CH₃ | C₄H₉ |
| C₂H₅ | CH₂F | CH₃ |
| FCH(CH₃) | CH₃ | C₂H₅ |
| FCH(CH₃) | C₃H₇ | CH₃ |
| FCH(CH₃) | CH₂Cl | C₂H₅ |
| FCH(CH₃) | CH₂F | CH₃ |
| ClCH(CH₃) | C₂H₅ | C₂H₅ |

-continued

| R¹ | R² | R³ |
|---|---|---|
| ClCH(CH₃) | CH₂F | CH₃ |
| ClCH(CH₃) | CH₂CN | CH₃ |
| CH₃COOCH(CH₃) | CH₃ | C₂H₅ |
| CH₃COOCH(CH₃) | CH₂F | CH₃ |
| CH₃COOCH(CH₃) | CH₂CN | CH₃ |
| p-O₂NC₆H₄CH₂OCOOCH(CH₃) | CH₂Cl | C₂H₅ |
| p-O₂NC₆H₄CH₂OCOOCH(CH₃) | CH₂CN | CH₃ |
| (CH₃)₃SiOCH(CH₃) | CH₃ | C₂H₅ |
| (C₂H₅)₃SiOCH(CH₃) | CH₃ | CH₃ |
| (C₂H₅)₃SiOCH(CH₃) | C₂H₅ | C₂H₅ |
| (C₂H₅)₃SiOCH(CH₃) | CH₂F | CH₃ |
| (C₂H₅)₃SiOCH(CH₃) | CH₂Cl | C₂H₅ |
| (CH₃)₃CSi(CH₃)₂OCH(CH₃) | CH₃ | CH₃ |
| (CH₃)₃CSi(CH₃)₂OCH(CH₃) | C₂H₅ | C₂H₅ |
| (CH₃)₃CSi(CH₃)₂OCH(CH₃) | CH₃ | C₃H₇ |
| (CH₃)₃CSi(CH₃)₂OCH(CH₃) | CH₃ | isoC₃H₇ |
| (CH₃)₃CSi(CH₃)₂OCH(CH₃) | CH₃ | cycC₆H₁₁ |
| (CH₃)₃CSi(CH₃)₂OCH(CH₃) | C₂H₅ | C₂H₅ |
| (CH₃)₃CSi(CH₃)₂OCH(CH₂) | CH₂F | CH₃ |
| (CH₃)₃CSi(CH₃)₂OCH(CH₃) | CH₂Cl | C₂H₅ |
| (CH₃)₃CSi(CH₃)₂OCH(CH₃) | CH₃ | C₃H₇ |
| (CH₃)₃CSi(CH₃)₂OCH(CH₃) | C₂H₅ | C₂H₅ |
| (CH₃)₃CSi(CH₃)₂OCH(CH₃) | CH₂F | CH₃ |
| (CH₃)₃CSi(CH₃)₂OCH(CH₃) | CH₂F | cycC₅H₉ |
| (CH₃)₃CSi(CH₃)₂OCH(CH₃) | CH₂F | cycC₆H₁₁ |
| (CH₃)₃CSi(CH₃)₂OCH(CH₃) | CH₂Cl | C₂H₅ |
| CH₂(CH₂O)₂C(CH₃) | CH₂CN | CH₃ |
| (CH₃)₃SiOCH(CH₃) | CH₃ | CH₃ |
| (CH₃)₃SiOCH(CH₃) | C₂H₅ | C₂H₅ |
| (CH₃)₃SiOCH(CH₃) | CH₂F | CH₃ |
| (CH₃)₃SiOCH(CH₃) | CH₂Cl | C₂H₅ |
| (CH₃)₃SiOCH(CH₃) | CH₂CN | C₂H₅ |
| (C₂H₅)₃SiOCH(CH₃) | CH₃ | C₂H₅ |
| (C₂H₅)₃SiOCH(CH₃) | C₂H₅ | CH₃ |
| (C₂H₅)₃SiOCH(CH₃) | CH₂F | C₂H₅ |
| (C₂H₅)₃SiOCH(CH₃) | CH₂CN | C₂H₅ |
| (C₂H₅)₃SiOCH(CH₃) | CH₂CH=CH₂ | C₃H₇ |
| (C₂H₅)₃SiOCH(CH₃) | CH₂CONH₂ | C₄H₉ |
| (C₂H₅)₃SiOCH(CH₃) | CH₂CH₂SCH₃ | CH₃ |
| (C₂H₅)₃SiOCH(CH₃) | CH₂CH₂OH | C₂H₅ |
| (C₂H₅)₃SiOCH(CH₃) | CH₂CH₂OCOCH₃ | C₂H₅ |
| C₃H₇ | CH₃ | CH₃ |
| C₃H₇ | C₂H₅ | C₂H₅ |
| C₃H₇ | CH₂F | C₂H₅ |
| C₃H₇ | CH₂Cl | C₂H₅ |
| C₃H₇ | CH₂CN | C₂H₅ |
| C₃H₇ | CH₂CH=CH₂ | C₃H₇ |
| CH₃CH(CH₃) | CH₂CONH₂ | C₄H₉ |
| CH₃CH(CH₃) | CH₂CH₂SCH₃ | CH₃ |
| CH₃CH(CH₂OOCOCH₃) | CH₂CH₂OH | C₂H₅ |
| CH₃CH(CH₂OOCOCH₃) | CH₂CH₂OCOCH₃ | C₂H₅ |
| CH₃CH(CH₂OOCOCH₃) | CH₃ | C₂H₅ |
| CH₂C(CH₂OC(C₆H₅)₃)₃ | C₂H₅ | CH₃ |
| CH₂C(CH₂OC(C₆H₅)₃)₃ | CH₂F | C₂H₅ |
| CH₂C(CH₂OC(C₆H₅)₃)₃ | CH₂Cl | C₂H₅ |

[Preparation of acrylic acids (III)]

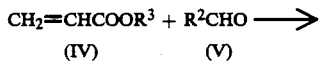

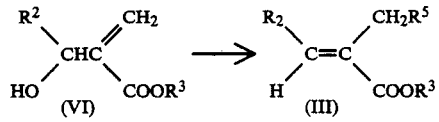

PREPARATION 1

R²=methyl, R³=methyl, R⁵=bromo.

In a manner to that of S. E. Drews, D. Emsley, et al., in J. Chem. Soc., Perkin Transaction I, pp. 2079 and 2079 (1982), an ice cooled solution of methyl acrylate (IV) (8.6 g) in conc. HBr (16.5 ml) is mixed dropwise with acetaldehyde (V) (4.4 g) and then conc. sulfuric acid (15 ml). After stirring overnight, the reaction mixture is extracted thrice with ether. The extract is washed with saturated saline, dried over MgSO₄, and concentrated. The resulting residue is distilled under reduced pressure to give methyl 2-bromomethyl-2-butenoate (III) (8.59 g). 83°~85° C./10 mmHg.

NMR (EM390, CDCl₃)δ: 1.94 (3H, d, J=6.5 Hz), 3.85 (3H, s), 4.27 (2H, s), 7.10 (1H, q, J=6.5 Hz) ppm.

PREPARATION 2

R²=methyl, R³=ethyl, R⁵=bromo.

In a manner similar to that of Preparation 1, ethyl acrylate (IV) is treated with acetaldehyde (V) to give ethyl 2-bromomethylbut-2-enoate (III). Yield: 59%. bp. 63°–65° C./1 mmHg.

NMR (EM390, CDCl₃)δ: 0.33 (3H, t, J=6.6 Hz), 0.90 (3H, d, J=6.5 Hz), 4.25 (2H, s), 4.26 (2H, q, J=6.6 Hz), 7.07 (1H, q, J=6.5 Hz) ppm.

PREPARATION 3

R²=ethyl, R³=methyl, R⁵=bromo.

In a manner similar to that of Preparation 1, methyl acrylate (IV) is treated with propionaldehyde (V) to give methyl 2-bromomethylpent-2-enoate (III). Yield: ca. 50%. bp. 80° C./7 mmHg.

[Experiments: Comparison with non-carboxy compounds]

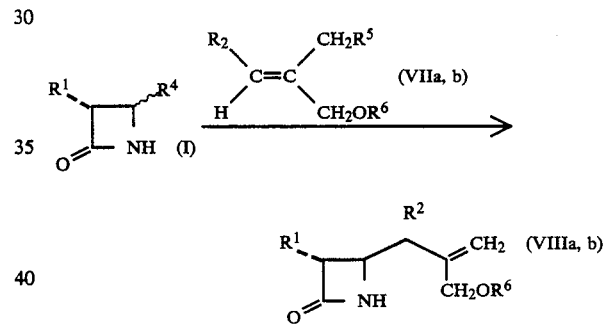

REFERENCE EXAMPLE 1

R¹=1-(tert-butyldimethylsilyloxy)ethyl, R²=methyl, R⁶=trityl, R⁴=acetoxy, R⁵=bromo.

To a stirred mixture of zinc powder (0.80 g) in tetrahydrofuran (20 ml) at room temperature is added cupric bromide (0.10 g) and stirred for 30 minutes to activate zinc. To this mixture is added a solution of acetate (I) (1.44 g) in tetrahydrofuran (10 ml) and then a solution of allyl bromide trityl ether (VIIa) (2.20 g) in tetrahydrofuran (10 ml) at ca. 35° C. during 30 minutes. After stirring the mixture for 2.5 hours, the reaction mixture is diluted with ethyl acetate and saturated saline, stirred and filtered to remove solid. The filtrate is washed with saline, dried (Na₂SO₄) and concentrated in vacuo. The residue is purified by chromatography (Lobar column B×2, tolunene:ethyl acetate=4:1) to afford 1(R)-methyl isomer of trityl ether adduct (VIIIa) (0.45 g; Yield: 16%) from the forerun. mp. 89°–91° C. (from acetone-n-hexane).

IR (Nujol)ν: 3452, 3172, 1762, 1733, 1725 cm⁻¹.

[α]²⁴_D 36.0°±0.8° (c, 1.012, CHCl₃).

NMR (EM390, CDCl₃)δ: 0.07 (ca. 6H, s), 0.85 (ca. 9H, s), 1.14 (3H, d, J=6 Hz), 1.15 (3H, J=7.2 Hz), 2.83 (1H, m), 2.86 (1H, dd, J=4.8 Hz, J=1.7 Hz), 3.42 (1H, brs), 3.77 (1H, dd, J=5.2 Hz, J=1.7 Hz), 4.10 (1H, qd, J=6.0, J=4.8 Hz), 6.72 (1H, brs) ppm.

From the later fractions, 1(S)-methyl isomer of trityl ether adduct (VIIIa) is obtained (0.50 g; Yield: 18%).

NMR (EM390, CDCl$_3$)δ: 0.85 (9H, s), 1.11 (3H, d, J=5.4 Hz), 1.17 (3H, d, J=6.5 Hz), 1.88–2.23 (1H, m), 2.55 (1H, d, J=6 Hz), 3.42 (1H, d, J=6.3 Hz), 3.53 (2H, brs), 3.93–4.23 (1H, m), 4.93 (1H, s), 5.32 (1H, s), 6.16 (1H, s), 7.06–7.47 (15H, m) ppm.

Allyl bromide trityl ether (VIIa) was prepared by reducing methyl 2-bromomethylbut-2-enoate (III) with diisobutylaluminum hydride followed by tritylating.

REFERENCE EXAMPLE 2

$R^1$ = 1-(tert-butyldimethylsilyloxy)ethyl, $R^2$ = methyl, $R^6$ = acetyl, $R^4$ = acetoxy, $R^5$ = bromo.

A mixture of zinc powder (0.80 g) and cupric bromide (0.10 g) in tetrahydrofuran (6 ml) is stirred at room temperature for 30 minutes. To this mixture is added a solution of acetate (I) (1.44 g) in tetrahydrofuran (2 ml) and then a solution of allyl bromide acetate (VIIb) (1.10 g) in tetrahydrofuran (5 ml) at ca. 35°~38° C. during 30 minutes. After stirring the mixture for 2 hours, the reaction mixture is treated as above and the obtained residue is purified by chromatography (Lobar column B×2, tolunene:ethyl acetate=4:1) to afford acetate adduct stereo-isomers (R, S-VIIIb) mixture (0.23 g). Total yield: 13%. By estimating from NMR spectra, the ratio of isomers at $R^2$ is about β:α≈5:2.

NMR (EM390, CDCl$_3$)δ: 0.90 (9H, s), 1.09–1.29 (6H, m), 2.25–2.55 (1H, m), 2.71 (ca. 2H/7, dd, J=4.5 Hz, J=2 Hz), 2.82 (ca. 5H/7, dd, J=4.5 Hz, J=3 Hz), 3.54 (ca, 2H/7, dd, J=9.5 Hz, J=2 Hz), 3.71 (ca. 5H/7, dd, J=6.6 Hz, J=3 Hz), 4.03–4.30 (1H, m), 4.56 (2H, s), 5.04 (1H, s), 5.17 (1H, s), 6.25 (ca. 2H/7, brs), 6.41 (ca. 5H/7, brs) ppm.

Allyl bromide acetate (VIIb) was prepared by reducing methyl 2-bromomethylbut-2-enoate (III) with diisobutylaluminum hydride followed by acetylating.

[References: Comparison with other condensations]

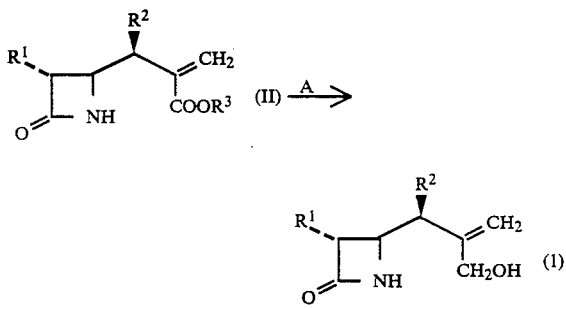

REFERENCE EXAMPLE 3

$R^1$ = 1-(tert-butyldimethylsilyloxy)ethyl, $R^6$ = trityl.

To a stirred solution of sodium hexamethyldisilazane (550 mg:3 equivalents) in tetrahydrofuran (5 ml) at −78° C. is added a solution of trityloxymethyl ethyl ketone (VIIc) (1.1 equivalents) in tetrahydrofuran (2.5 ml) over 15 minutes and then stirred for 10 minutes. Then, a solution of acetate (I) (287 mg:1 millimole) in tetrahydrofuran (2.5 ml) is added to the mixture. After 5 minutes at the same temperature, the reaction mixture is diluted with saturated aqueous ammonium chloride and extracted with ethyl acetate. The extract solution is washed with water, dried, and concentrated in vacuum. The residue is purified by silica gel chromatography (Lober B, toluene-ethyl acetate=2:1) to give α-methyl derivative of the adduct (VIIIc) (79 mg; Yield: 14.9%) from non-polar fraction.

mp 130°–131° C. (from n-hexane).

Elemental analysis: ($C_{34}H_{43}NO_4Si$) Calcd.: C, 73.21; H, 7.77; N, 2.51. Found: C, 73.19; H, 7.75; N, 2.53.

$[\alpha]^{23}_D$ −6.9°±0.5° (c, 1.014 in CHCl$_3$).

IR (Nujol)ν: 3080, 3060, 1762, 1727 cm$^{-1}$.

NMR (EM390, CDCl$_3$)δ: 0.87 (9H, s), 1.11 (3H, d, J=6.9 Hz), 1.20 (3H, d, J=6.0 Hz), 2.56–2.90 (2H, m), 3.65 (1H, dd, J=9.8, J=1.8 Hz), 3.90 (2H, s), 4.11 (1H, quintet, J=6 Hz), 5.73 (1H, br), 7.07–7.50 (15H, m) ppm.

The β-methyl derivative of the adduct (VII) (132 mg; Yield: 24.8% ) is obtained from highly polar fraction.

mp 133°–134° C. (from n-hexane-acetone).

$[\alpha]^{23}_{365}$ −18.5°±0.5° (c, 1.000 in CHCl$_3$).

IR (Nujol)ν: 3240, 3080, 1765, 1727, 1716 cm$^{-1}$.

[Reaction A: Reduction]

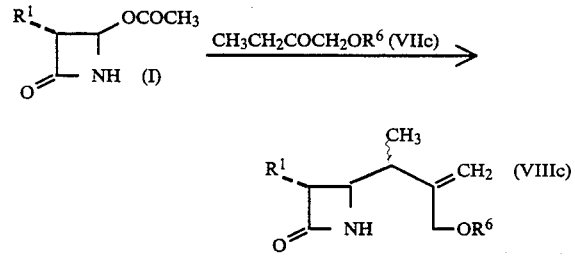

EXAMPLE A-1

$R^1$ = 1-(tert-butyldimethylsilyloxy)ethyl, $R^2$ = methyl, $R^3$ = methyl.

To a solution of methyl ester (II) (15.5 g) in toluene (150 ml) at −20° C. is dropwise added a solution of 1N-diisobutylaluminum hydride in toluene (140 ml) over 30 minutes. After stirring under ice cooling for 30 minutes, the reaction mixture is poured into ice water, stirred for 30 minutes, and filtered to remove solid. The toluene layer is washed with water, dried (MgSO$_4$), and concentrated in vacuum to give crude crystals of alcohol (1) (16.0 g). mp. 82°–83° C. (from ether-n-hexane).

IR (Nujol)ν: 3364, 3160, 3084, 1756, 1721, 1712, 1649, 1645, 1134, 1043, 1030, 832 cm$^{-1}$.

NMR (VXR200, CDCl$_3$)δ: 0.07 (6H, s), 0.88 (9H, s), 1.14 (3H, d, J=7.0 Hz), 1.20 (3H, d, J=6.2 Hz), 1.80 (ca. 1H, brs), 2.45 (1H, quintet, J=7 Hz), 2.89 (1H, m), 3.69 (1H, dd, J=6.0 Hz, J=1.9 Hz), 4.13 (2H, s), 4.10–4.19 (1H, m), 4.98 (1H, s), 5.17 (1H, d, J=1.0 Hz), 6.10 (1H, brs) ppm.

$[\alpha]^{23}_D$ −33.2° (c, 1.014 in CHCl$_3$).

Elemental analysis: ($C_{16}H_{31}NO_3Si$) Calcd.: C, 61.30; H, 9.97; N, 4.47. Found: C, 61.23; H, 10.04; N, 4.46.

EXAMPLE A-2

$R^1$ = 1-(tert-butyldimethylsilyloxy)ethyl, $R^2$ = methyl, $R^3$ = ethyl.

In a manner similar to that of methyl ester, ethyl ester (II) is reduced with diisobutylaluminum hydride to give crystals of the same alcohol (1) as obtained in Example A-1.

IR ν (Nujol): 3364, 3160, 3084, 1756, 1721, 1712, 1649, 1645, 1134, 1043, 1030, 832 cm$^{-1}$.

EXAMPLE A-3

R¹=1-(tert-butyldimethylsilyloxy)ethyl, R²=ethyl, R³=methyl, R⁶=trityl.

In a manner similar to that of preceding methyl derivative, ethyl derivative (II) (3.54 g; 10 millimoles) is reduced with diisobutylaluminum hydride to give alcohol (1). The product was identified as trityl ether by treating with trityl chloride and triethylamine to give crystalline trityl ether (2) (5.00 g). Yield: 87%.

NMR (VXR200, CDCl₃)δ: 0.02 (ca. 6H, s), 0.83 (9H, s), 0.86 (3H, t, J=4.5 Hz), 1.01 (3H, d, J=6.4 Hz), 1.19–1.48 (2H, m), 2.64 (1H, t, J=2.7 Hz), 3.44 and 3.56 (2H, ABq, J=13 Hz, J=4 Hz), 3.51–3.54 (1H, m), 4.09 (1H, dq, J=6.4 Hz, J=3.5 Hz), 5.03 (1H, brs), 5.54 (1H, brs), 5.75 (1H, brs), 7.15–7.48 (15H, m) ppm.

[Reaction B: Protection at alcohol]

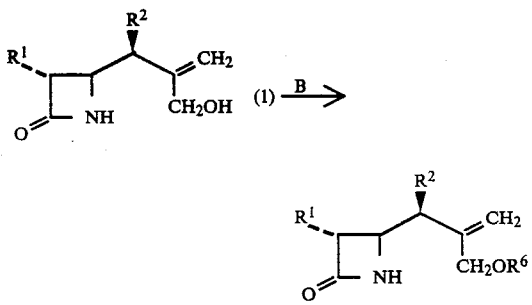

EXAMPLE B-1 (TRITYL)

R¹=1-(tert-butyldimethylsilyloxy)ethyl, R²=methyl, R⁶=trityl.

To an ice cooled solution of alcohol (1) (16.0 g) and trityl chloride (15.0 g) in dichloromethane (120 ml) is added triethylamine (20 ml). The mixture is kept overnight at room temperature. The reaction mixture is washed with water, dried (MgSO₄), and concentrated in vacuum. The residue is crystallized from n-hexane to give trityl ether (2) (20.7 g). Yield: 82%. mp. 147°–148° C.

IR (Nujol)ν: 3200, 1754, 1713, 1654, 1600, 1490 cm⁻¹.

NMR (VXR-200, CDCl₃)δ: 0.03 (ca. 6H, s), 0.83 (9H, s), 1.03 (3H, d, J=7.0 Hz), 1.08 (3H, d, J=6.4 Hz), 2.30 (1H, quintet, J=6.6 Hz), 2.69 (1H, dd, J=4.3 Hz, J=2.2 Hz), 3.58 (1H, dd, J=6.2, J=2.2 Hz), 3.51, 3.60 (2H, ABq, J=20 Hz), 4.09 (1H, dq, J=6.4 Hz, J=4.3 Hz), 5.01 (1H, s), 5.40 (1H, d, J=1.4 Hz), 5.65 (1H, s), 7.26–7.47 (15H, m) ppm.

[α]²³_D −11.5° (c, 1.008 in CHCl₃).

Elemental analysis: (C₃₅H₄₅NO₃Si) Calcd.: C, 75.63; H, 8.16; N, 2.52. Found: C, 75.71; H, 8.15; N, 2.54.

EXAMPLE B-2 (TRITYL)

R¹=1-(tert-butyldimethylsilyloxy)ethyl, R²=ethyl, R⁶=trityl.

The alcohol (1) of Example A-3 (3.54 g) is treated with trityl chloride and triethylamine analogously to Example B-1 to give crystalline trityl ether (2) (5.00 g). Yield: 87%. NMR (VXR-200, CDCl₃)δ: 0.02 (ca. 6H, s), 0.83 (9H, s), 0.86 (3H, t, J=4.5), 1.01 (3H, d, J=6.4 Hz), 1.19–1.48 (2H, m), 2.64 (1H, t, J=2.7 Hz), 3.44, 3.56 (2H, ABq, J=13 Hz, J=4 Hz), 3.51–3.54 (1H, m), 4.09 (1H, dq, J=6.4 Hz, J=3.5 Hz), 5.03 (1H, brs), 5.54 (1H, brs), 5.75 (1H, brs), 7.15–7.48 (15H, m) ppm.

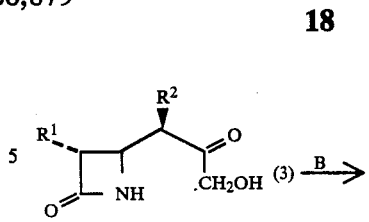

EXAMPLE B-3 (acetyl)

R¹=1-(tert-butyldimethylsilyloxy)ethyl, R²=methyl, R⁶=acetyl

Ketol (3) or its isomer at R² is treated with acetyl chloridetriethylamine at −30° to −40° C. to give acetate (3) (α-methyl) (IR(Nujol)ν: 3420, 3360, 1776, 1760, 1740, 1580, 1252, 1220 cm⁻¹) or acetate (3) (β-methyl).

Elemental analysis: (C₁₇H₃₁NO₅Si) Calcd.: C, 57.11; H, 8.74; N, 3.92. Found: C, 57.01; H, 8.84; N, 4.02.

[α]²⁴_D −15.9°±0.6° (c, 0.996 in CHCl₃).

IR (Nujol)ν: 3440, 3200, 1766, 1752, 1737, 1730, 1230 cm⁻¹.

NMR (EM-390,CDCl₃)δ: 0.83 (9H, s), 1.11 (3H, d, J=6 Hz), 1.12 (3H, d, J=7.2 Hz), 2.08 (3H, s), 2.60–2.96 (1H, m), 2.84 (1H, dd, J=4.8 Hz, J=2.0 Hz), 3.78 (1H, dd, J=5.5 Hz, J=2.0 Hz), 4.07 (1H, quintet, J=6 Hz), 4.62 (2H, s), 6.47 (1H, brs) ppm.

EXAMPLE B-4 (silyl in R⁶)

R¹=1-(tert-butyldimethylsilyloxy)ethyl, R²=methyl, R⁶=tert-butyldimethylsilyl.

To a solution of ketol (3) (180 mg; 0.57 millimoles) in dimethylformamide (0.3 ml) are added tert-butyldimethylsilyl chloride (130 mg; 1.5 equivalents) and imidazole (100 mg; 2.5 equivalents). After keeping at room temperature overnight, the reaction mixture is poured into ethyl acetate-ice water. The organic layer is separated, washed with water, dried (MgSO₄), and concentrated in vacuum. The crystalline residue is purified by silica gel chromatography (Lobar B, toluene-ethyl acetate=4:1) to give crystalline tert-butyldimethylsilyl ether (3) (225 mg). Yield: 91.8%.

IR (CCl₄)ν: 3420, 3200, 1777, 1718, 1580 cm⁻¹.

NMR (EM-390, CDCl₃)δ: 0.86 (9H, s), 0.93 (9H, s), 1.14 (3H, d, J=7.3 Hz), 1.18 (3H, d, J=6 Hz), 2.89 (1H, dd, J=4.8 Hz, J=2.3 Hz), 3.20 (1H, qd, J=7.3 Hz, J=4.5 Hz), 3.82 (1H, dd, J=4.5 Hz, J=2.3 Hz), 4.16 (1H, qd, J=6 Hz, J=2.3 Hz), 5.93 (1H, brs) ppm.

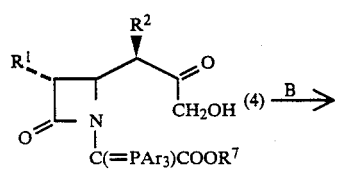

-continued

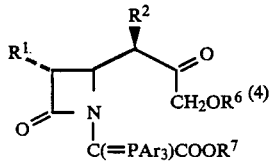

EXAMPLE B-5 (acetyl, silyl in R¹)

$R^1$ = 1-hydroxyethyl→1-(triethylsilyloxy)ethyl, $R^2$ = methyl, $R^6$ = acetyl, $R^7$ = p-methoxybenzyl, Ar = phenyl (1) Acetyl as $R^6$: To a solution of ketol (4) (6.97 g) (10.9 millimoles) in dichloromethane at −40° C. are dropwise added triethylamine (2.3 ml; 1.5 equivalents) and acetyl chloride (1.2 ml; 1.5 equivalents), and the mixture is stirred for 3 hours to give a solution of acetate (4).

(2) Silyl in $R^1$: To this solution of acetate (4) are added triethylsilyl chloride (4.6 ml; 2.5 equivalents) and triethylamine (3.8 ml; 2.5 equivalents). After stirring at 0° C. for 3 hours, the reaction mixture is poured into ice water. The organic layer is separated and processed in a usual manner to give triethylsilylate (4).

This product (4) in methanol (30 ml) is hydrolyzed with 5.2 N-sodium methylate in methanol (1.2 ml; 0.57 equivalents) at −50° C. for 3 hours as in Example B'-8 to give alcohol (4). This product (4) is heated in toluene (300 ml) at 110° C. for 15 minutes as in Example E-4 to give 1-carbapen-2-em (a) (3.7 g). Yield: 71%.

EXAMPLE B-6 (mesyl)

$R^1$ = 1-(triethylsilyloxy)ethyl→1-hydroxyethyl, $R^2$ = ethyl, $R^7$ = p-methoxybenzyl, $OR^6$ = OH→O-mesyl→HetS, Ar = phenyl, Het = 4-pyridyl.

To a solution of ketol (4) (4.41 g; 5.74 millimoles) in dichloromethane (22 ml) at −60° C. under nitrogen are added dropwise methanesulfonyl chloride (0.49 ml; 1.1 equivalents) and triethylamine (1.84 ml; 2.3 equivalents). After stirring for 1 hour, mesylate (4) is obtained.

This product (4) is reacted with 4-mercaptopyridine (803 mg; 1.25 equivalents) in acetonitrile (22 ml) as in Example F-1 to give pyridyl sulfide (7). The silyl is removed with concentrated hydrochloric acid (3.2 ml; 6.5 equivalents) in acetic acid (6 ml) at 0° C. as in Example B'-10 to give alcohol (7) (3.52 g). Total Yield: 82%.

IR (CHCl₃)ν: 3620-3300, 1745, 1720 sh, 1619, 1582 cm⁻¹.

EXAMPLE B-7 (mesyl)

$R^1$ = 1-hydroxyethyl, $R^2$ = ethyl, $R^6$ = methanesulfonyl, $R^7$ = p-methoxybenzyl, Het = 4-pyridyl.

To a solution of ketol (4) (600 mg; ca. 0.81 millimoles) in dichloromethane (4 ml) at −50° C. under nitrogen are dropwise added methanesulfonyl chloride (0.08 ml; ca. 1.3 equivalents) and triethylamine (0.3 ml; 2.6 equivalents) to give mesylate (4).

This product (4) is treated with 4-mercaptopyridine (129 mg; 1.4 equivalents) in acetonitrile (2 ml) at 0° C. for 1 hour to give pyridylthioylide (7) as in Example F-3. This is heated in toluene (35 ml) at 110° C. for 1 hour as in Example E-8 to give 6α-(1-hydroxyethyl)-1-ethyl-2-(4-pyridylthio)methyl-1-carbapen-2-em-3-carboxylic acid p-methoxybenzyl ester (b) {86 mg; IR (CHCl₃)ν: 3680, 3604, 1772, 1712, 1612, 1586 cm⁻¹, Yield: 22.8%} and two other products.

EXAMPLE B-8 (chloro)

$R^1$ = 1-hydroxyethyl, $R^2$ = methyl, $OR^6$ = Cl→SHet, $R^7$ = allyl, Ar = phenyl, Het = 4-pyridyl.

To a stirring solution of ketol (4) (9.52 g; 17 millimoles) in acetonitrile (85 ml) are added carbon tetrachloride (34 ml) and triphenylphosphine (5.4 g; 1.2 equivalents) in small portions with stirring under ice cooling over 2 hours to give a solution of chloride (4).

This product (4) is treated with 4-mercaptopyridine (2.45 g; 1.3 equivalents) and sodium carbonate (1.8 g; 1 equivalents) at room temperature for 2 hours to give 4-pyridyl sulfide (7) (7.87 g) as in Example F-2. Yield: 71%.

IR (CHCl₃)ν: 3100-2900, 1735, 1707, 1610, 1430 cm⁻¹.

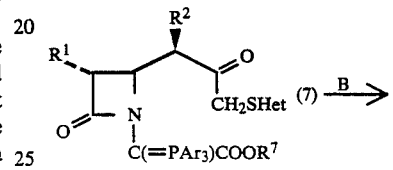

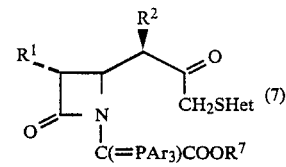

EXAMPLE B-9 (silyl in R¹)

$R^1$ = 1-hydroxyethyl→1-(tert-butyldimethylsilyloxy)ethyl, $R^2$ = ethyl, $R^7$ = p-methoxybenzyl, Het = 4-pyridyl To a stirring solution of alcohol (7) (1.00 g; 1.34 millimoles) in dichloromethane (10 ml) at 0° C. is dropwise added a solution of triethylsilyl chloride (0.32 ml; 1.4 equivalents) and triethylamine (0.28 ml; 1.5 ml) in dichloromethane (5 ml) over 20 minutes. After stirring for 2 hours at the same temperature, the reaction mixture is poured into iced water. The formed organic layer is separated, washed with water, dried, and concentrated in vacuum. The residue is purified by silica gel chromatography (Lober B, toluene-ethyl acetate = 1:1) to give triethylsilyl ether (7) (984 mg). Yield: 85.3%.

IR (CHCl₃)ν: 1740, 1715, 1610, 1576 cm⁻¹.

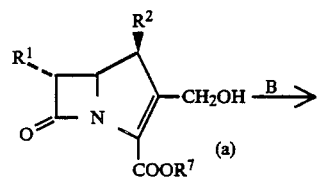

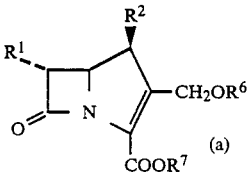

EXAMPLE B-10 (chloro)

$R^1$=1-(triethylsilyloxy)ethyl, $R^2$=methyl, $OR^6$=Cl→SHet, $R^7$=p-methoxybenzyl, Het=4-pyridyl.

To a solution of alcohol (a) (800 mg; 1.68 millimoles) in dichloromethane (10 ml) at −60° C. with stirring are dropwise added 4-(dimethylamino)pyridine (40 mg; 0.2 equivalents), triethylamine (0.28 ml; 1.2 equivalents), and diphenyl chlorophosphate (0.42 ml; 1.2 equivalents). After 30 minutes' stirring, the mixture is treated with trimethylsilyl chloride (0.75 ml; 3.9 equivalents) and stirred for 1 hour to give a chloride of (a, $R^6$=H).

This chloride (a) is treated with 4-mercaptopyridine (280 mg; 1.5 equivalents) and triethylamine (0.35 ml; 1.5 equivalents) in acetonitrile (10 ml) for 1 hour at −20° C. as in Example F-4 to give 4-pyridyl sulfide (b) (680 mg). Yield: 71.6%.

EXAMPLE B-11 (diphenyl phosphate)

$R^1$=1-hydroxyethyl, $R^2$=methyl, $OR^6$=OPO(OPh)$_2$→SHet, $R^7$=p-methoxybenzyl, Het=4-pyridyl.

To a solution of diol (a) 5.42 g (15.0 millimoles) and dimethylaminopyridine (550 mg; 0.3 equivalents) in dichloromethane (20 ml) stirring at −70° C. is dropwise added a solution of triethylamine (2.1 ml; 1.1 equivalents) and diphenyl chlorophosphate (3.1 ml) in dichloromethane (10 ml) over 15 minutes. The mixture is stirred for 1 hour to give a solution of diphenyl phosphate (a).

This product (a) is treated with 4-mercaptopyridine (2.00 g; 1.2 equivalents), triethylamine (2.1 ml; 1.1 equivalents), sodium iodide (2.7 g; 1.2 equivalents), and dimethylformamide (30 ml) at room temperature for 2 hours as in Example F-5 to give 4-pyridyl sulfide (b) (2.30 g). Yield: 33.7%.

IR (CHCl$_3$)ν: 3370–3130br, 1766, 1708, 1614, 1580 cm$^{-1}$.

EXAMPLE B-12 (diphenyl phosphate)

$R^1$=1-(tertbutyldimethylsilyloxy)ethyl, $R^2$=methyl, $OR^6$=OPO(OPh)$_2$→SHet, $R^7$=p-methoxybenzyl, Het=4-pyridyl.

To a solution of diol (a) (4.28 g; 9.0 millimoles) and dimethylaminopyridine (550 mg; 0.3 equivalents) in dimethylformamide stirring at −70° C. is dropwise added a solution of triethylamine (2.1 ml; 1.1 equivalents) and diphenyl chlorophosphate (3.1 ml) in dichloromethane (10 ml) over 15 minutes. The mixture is stirred for 1 hour to give a solution of diphenyl phosphate (a).

This product (a) is treated with 4-mercaptopyridine (1.2 equivalents), triethylamine (1.1 equivalents), sodium iodide (1.2 equivalents) and dimethylformamide (30 ml) at room temperature for 2 hours as in Example F-6 to give the corresponding 4-pyridyl sulfide (b) (4.4 g) in 85% yield. This (b) (2.1 g; 3.69 millimoles) in tetrahydrofuran (10 ml) is treated with acetic acid (0.8 ml) and tetrabutylammonium fluoride trihydrate (2.78 g; 2.4 equivalents) at room temperature for two nights as in Example B'-12 to give 6α-(1-hydroxyethyl)-1-methyl-2-(4-pyridylthio)methyl-1-carbapen-2-em-3-carboxylic acid p-methoxybenzyl ester (b) (455 mg; Y=27.1%; Constants given below) and its exo isomer (i.e., 6α-(1-hydroxyethyl)-1-methyl-2-(4-pyridylthio)methylene-1-carbapenam-3-carboxylic acid p-methoxybenzyl ester, 100 mg; Yield: 6.0%).

IR (CHCl$_3$)ν: 3400–3120br, 1750br, 1604, 1575 cm$^{-1}$.
NMR (EM-390, CDCl$_3$)Γ: 1.11 (3H, d, J=7.5 Hz), 1.35 (3H, d, J=6.3 Hz), 3.05–3.40 (ca. 3H, m), 4.02 (1H, dd, J=6.3 Hz, J=2 Hz), 4.23 (1H, quintet, J=6.3 Hz), 4.98 (1H, brs), 5.09, 5.24 (2H, ABq, J=11.3 Hz), 6.33 (1H, brs), 6.81, 7.28 (4H, ABq, J=8.4 Hz), 6.91, 8.35 (4H, ABq, J=5.5 Hz) ppm.

[Reaction B': Deprotection at alcohol]

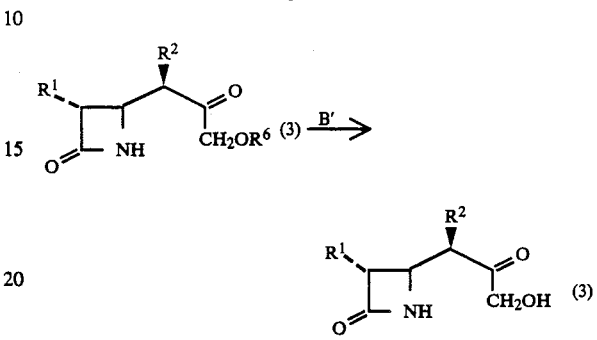

EXAMPLE B'-1 (trityl)

$R^1$=1-(tert-butyldimethylsilyloxy)ethyl, $R^2$=methyl, $R^6$=trityl.

To a solution of trityl ether (3) (110 mg; 0.207 millimoles) in dichloromethane (1.1 ml) at 0° C. is added a solution of 2.8N-hydrogen chloride in ethyl acetate (0.11 ml; 1.5 equivalents). After stirring for 30 minutes, the reaction mixture is poured into cold aqueous sodium hydrogen carbonate. The organic layer is separated, washed with water, dried, and concentrated in vacuum. The residue is purified by silica gel chromatography (Lober A, ethyl acetate) to give ketol (3). Yield: 70%. mp. 89°–91° C. (from acetone-n-hexane).

EXAMPLE B'-2 (trityl, silyl in $R^1$)

$R^1$=1-(tert-butyldimethylsilyloxy)ethyl→1-hydroxyethyl, $R^2$=methyl, $R^6$=trityl.

To a solution of silylated trityl ether (3) (110 mg; 0.207 millimoles) in dichloromethane (1.1 ml) at 0° C. is added a solution of 2.8N-hydrogen chloride in ethyl acetate (0.11 ml; 1.5 equivalents). After one night, the reaction mixture is poured into cold aqueous sodium hydrogen carbonate. The organic layer is separated, washed with water, dried, and concentrated in vacuum. The residue is purified by silica gel chromatography (Lober A, ethyl acetate) to give ketol (3). Yield: 65%.

IR (CHCl$_3$)ν: 3500–3250br, 1760, 1740, 1580, 1580 cm$^{-1}$.

EXAMPLE B'-3 (acetyl)

$R^1$=1-(tert-butyldimethylsilyloxy)ethyl, $R^2$=methyl, $R^6$=acetyl.

To a solution of acetate (3) (190 mg; 0.53 millimoles) in methanol (1.9 ml) at −20° C. is added 5.18N-sodium methylate (20 μl; 0.2 equivalents) and kept at −20° C. overnight. Then, a solution of 2.8N-hydrochloric acid-acetic acid (40 μl; 0.2 equivalents) is added, concentrated in vacuum, and obtained residue is purified by silica gel chromatography (Lober C, ethyl acetate-acetonitrile=9:1) to give ketol (3) (160 mg). Yield: 95.2%. mp 89°–91° C. (from acetone-n-hexane).

Similarly, the ketol of α-methyl derivative is prepared. Yield: 70%. mp 105°–107.5° C. (n-hexane).

Elemental analysis: Calcd.: C, 56.46; H, 9.29; N, 4.39. ($C_{15}H_{29}NO_4Si \cdot 1/10\ C_6H_{14}$) Found: C, 56.45; H, 9.54; N, 4.50.

$[\alpha]^{24}_D -16.7° \pm 1.1°$ (c, 0.509 in $CHCl_3$).

NMR (EM-390, $CDCl_3$)δ: 0.87 (9H, s), 1.17 (3H, d, J=3 Hz), 1.19 (3H d, J=2 Hz), 2.44–2.87 (2H, m), 3.21 (1H, brs), 3.77 (1H, dd, J=9.6 Hz, J=2.1 Hz), 4.16 (1H, m), 4.30 (2H, brs), 6.32 (1H, brs) ppm.

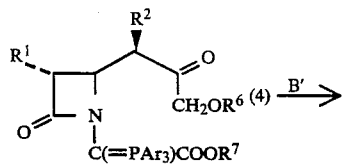

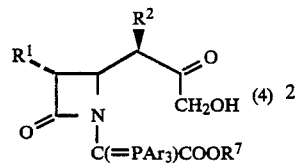

EXAMPLE B'-4 (trityl)

$R^1$ = 1-(tert-butyldimethylsilyloxy)ethyl, $R^2$=methyl, $R^6$=trityl, $R^7$=p-methoxybenzyl, Ar=-phenyl.

To a solution of tritylate (4) (620 mg; 0.622 millimoles) in dichloromethane (6.2 ml) at −25° C. under nitrogen is added a solution of 2.8N hydrogen chloride in ethyl acetate (0.28 ml; 1.26 equivalents). After one night, the reaction mixture is poured into aqueous sodium hydrogen carbonate. The organic layer is separated, dried, and concentrated in vacuum. The residue is purified by silica gel chromatography (Lober B, ethyl acetate) to give ketol (4) (331 mg). Yield: 71%.

IR ($CHCl_3$)ν: 3270br, 1764, 1750, 1724sh, 1610, 1584, 1515 $cm^{-1}$.

EXAMPLE B'-5 (trityl)

$R^1$ = 1-(tert-butyldimethylsilyloxy)ethyl, $R^2$=ethyl, $R^6$=trityl, $R^7$=p-methoxybenzyl, Ar=phenyl.

To a solution of tritylate (4) (12.7 g; 12.57 millimoles) in dichloromethane (55 ml) at −20° C. is added 3N-hydrogen chloride in ethyl acetate (10.5 ml; 2.5 equivalents). After stirring for 4 hours under ice cooling, the reaction mixture is poured into aqueous sodium hydrogen carbonate. The organic layer is separated, dried, and concentrated in vacuum. The residue is purified by silica gel chromatography (Lober C, acetonitrile) to give ketol (4) (5.87 g). Yield: 60.9%.

mp 98°–101° C. (from benzene-n-hexane).

IR (Nujol)ν: 3440, 1740, 1728, 1595, 1511, 1240 $cm^{-1}$.
$[\alpha]^{23}_D -40.5° \pm 0.8°$ (c, 1.012 in $CHCl_3$).

Elemental analysis: Calcd.: C, 65.73; H, 7.27; N, 1.74; P, 3.85. ($C_{44}H_{54}NO_7PSi$) Found: C, 66.10; H, 6.79; N, 1.80; P, 4.14.

EXAMPLE B'-6 (trity, silyl in $R^1$)

$R^1$ = 1-(tert-butyldimethylsilyloxy)ethyl→1-hydroxyethyl, $R^2$=methyl, $R^6$=trityl, $R^7$=p-methoxybenzyl, Ar=phenyl.

To an ice cold stirring suspension of silyl-tritylate (4) (22.5 g; 22.58 millimoles) in acetonitrile (70 ml) is dropwise added hydrochloric acid (9.4 ml; 5 equivalents). After 1 hour at the same temperature, the reaction mixture is poured into a mixture of toluene and water. The aqueous layer is separated and poured to cold aqueous sodium hydrogen carbonate-ethyl acetate. The organic layer is separated, washed with water, dried (MgSO4), and concentrated in vacuum to give ketol (4) (13.98 g) as colorless foam. Yield: 96.9%. IR ($CHCl_3$)ν: 3500–3250, 1760, 1740, 1580 $cm^{-1}$.

EXAMPLE B'-7 (trityl, silyl in $R^1$)

$R^1$ = 1-(tert-butyldimethylsilyloxy)ethyl→1-hydroxyethyl, $R^2$=methyl, $R^6$=trityl, $R^7$=allyl, Ar=phenyl.

To an ice cold stirring suspension of silylated trifylate (4) (7.22 g; 7.88 millimoles) in acetonitrile (24 ml) is dropwise added concentrated hydrochloric acid (2 ml; 3 equivalents). After 1 hour, the reaction mixture is washed with toluene, made basic with sodium hydrogen carbonate, and extracted with toluene. The extract solution is treated in a conventional manner to give ketol (4) (4.32 g). Yield: 98%.

IR ($CHCl_3$)ν: 3600–3200, 2980, 1740, 1705, 1620, 1440, 1108, 908 $cm^{-1}$.

NMR ($CDCl_3$)ν: 0.96 (3H, d, J=6.0 Hz), 1.46 (3H, d, J=6.8 Hz), 5.82–6.05 (1H, m), 7.1–7.9 (m) ppm.

EXAMPLE B'-8 (acetyl)

$R^1$ = 1-hydroxyethyl→1-(triethylsilyloxy)ethyl, $R^2$=methyl, $R^7$=p-methoxybenzyl, $R^6$=acetyl, Ar=phenyl.

Diol (4) (6.97 g; 10.9 millimoles) is acetylated with acetyl chloride (1.2 ml; 1.5 equivalents) and triethylamine (2.3 ml; 1.5 equivalents) in dichloromethane at −40° C. for 3 hours and silylated with triethylsilyl chloride (4.6 ml; 2.5 equivalents) and triethylamine (3.8 ml; 2.5 equivalents) at 0° C. for 3 hours as in Example B-5 to give starting silylated acetate (4).

To a solution of silylated acetate (4) in methanol (30 ml) at −50° C. is added dropwise 5.2N-sodium methylate in methanol (1.2 ml; 0.57 equivalents). After stirring for 3 hours, the mixture is neutralized with 1N-hydrochloric acid (7.3 ml). The reaction mixture is poured into ethyl acetate-water and extracted. The extract solution is washed with water, dried and concentrated in vacuum to give silylated ketol (4).

This product (4) is heated in toluene (300 ml) at 110° C. for 15 minutes as in Example E-4 to give 1-carbapen-2-em (a) (3.7 g). Yield: 71%.

NMR (VXR-200, $CDCl_3$)δ: 0.53–0.65 (6H, m), 0.90–0.99 (9H, m), 1.18 (3H, d, J=7.4 Hz), 1.27 (3H, d, J=6 Hz), 3.10–3.28 (1H, m), 3.22 (1H, dd, J=6.4 Hz, J=3.0 Hz), 3.80 (3H, s), 4.15 (1H, dd, J=10 Hz, J= 3 Hz), 4.36, 4.48 (2H, ABqd, $J_{AB}$=12 Hz, $J_{CH2:OH}$=6 Hz), 5.23 (2H, s), 6.89, 7.39 (4H, $A_2B_2$q, J=8.8 Hz) ppm.

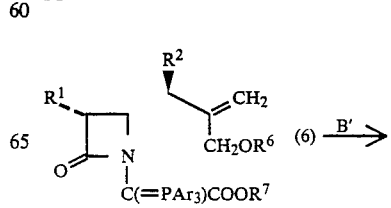

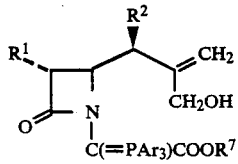

EXAMPLE B'-9 (trityl, silyl in R¹)

R¹=1-(tert-butyldimethylsilyloxy)ethyl→1-hydroxyethyl, R²=methyl, R⁶=trityl, R⁷=p-methoxybenzyl.

To a suspension of silylated trityl ether (6) (1.05 g; 1.06 millimoles) in acetonitrile (5 ml) is added concentrated hydrochloric acid (0.44 ml; ca. 5 equivalents) and acetic acid (0.2 ml) under ice cooling. After stirring for 1 hour the reaction mixture is poured into cold aqueous sodium hydrogen carbonate-ethyl acetate, and extracted. The extract solution is washed with water, dried, and concentrated in vacuum. The residue is purified by silica gel chromatography (Lober B, ethyl acetate) to give diol (6) (676 mg). mp 90°-92° C. (from etherpetroleum ether). Yield: 100%.

IR (Nujol)$\nu$: 3350(br), 1736, 1728(sh), 1611br, 1512, 1240 cm⁻¹.

Elemental analysis: Calcd.: C, 70.57; H, 6.39; N, 2.17; P, 4.79. ($C_{38}H_{40}NO_6P \cdot \frac{1}{2}H_2O$) Found: C, 70.41; H, 6.45; N, 2.40; P, 5.02.

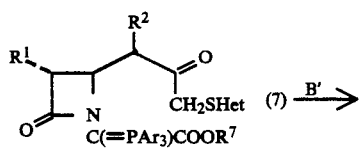

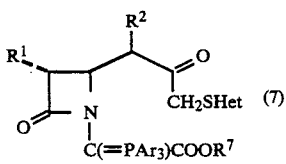

EXAMPLE B'-10 (silyl in R¹)

R¹=1-(triethylsilyloxy)ethyl→1-hydroxyethyl, R²=ethyl, OR⁶=O-mesyl→SHet, R⁷=p-methoxybenzyl, Ar=phenyl, Het=4-pyridyl.

Silylate (4) (4.41 g; 5.74 millimoles) in dichloromethane (22 ml) at −60° C. is esterified with methanesulfonyl chloride (0.49 ml; 1.1 equivalents) and triethylamine (1.84 ml; 2.3 equivalents) at room temperature for 1 hour as in Example B-10 to give mesylate (4). This (4) is treated with 4-mercaptopyridine (803 mg; 1.25 equivalents) at room temperature in acetonitrile (22 ml) for 2 hours as in Example F-6 to give starting pyridylsulfide (7) (4.4 g). Yield: 85%.

A solution of this pyridylsulfide (7) in acetonitrile (22 ml) is mixed with concentrated hydrochloric acid (3.2 ml; 6.5 equivalents) and acetic acid (6 ml) at 0° C., stirred for 2 hours, poured into aqueous sodium hydrogen carbonate, and extracted at pH 6.5 with dichloromethane. The extract solution is washed with water, dried, and concentrated in vacuum. The residue is purified by chromatography (Lober B, ethyl acetate-acetonitrile (9:1 to 1:1) over silica gel to give hydroxypyridylthioylide (7) (3.52 g). Yield: 82%.

IR (CHCl₃)$\nu$: 3620-3300, 1745, 1720sh, 1619, 1582 cm⁻¹.

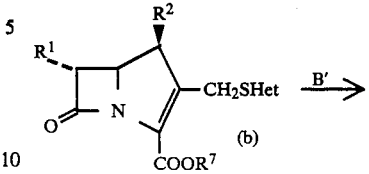

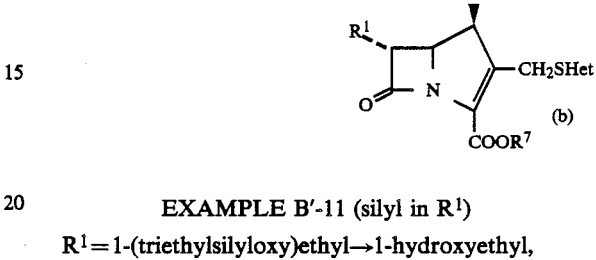

EXAMPLE B'-11 (silyl in R¹)

R¹=1-(triethylsilyloxy)ethyl→1-hydroxyethyl, R²=ethyl, R⁷=p-methoxybenzyl, Het=4-pyridyl.

To a solution of triethylsilyl ether (b) (582 mg; 1 millimoles) in tetrahydrofuran (3 ml) at 0° C. under nitrogen at 0° C. is added a solution of acetic acid (0.34 ml; 6 equivalents) and 1M-tetrabutylammonium fluoride in tetrahydrofuran (4.5 ml; 4.5 equivalents). After one night, the reaction mixture is poured into aqueous sodium hydrogen carbonate-ethyl acetate. The organic layer is washed with water, dried, and concentrated in vacuum. The residue is purified by silica gel chromatography (Lober B, acetonitrile-ethyl acetate 1:1) to give alcohol (b) (446 mg). Yield: 95.3%.

NMR (VXR-200, CDCl₃)$\delta$: 1.04 (3H, t, J=7.4 Hz), 1.35 (3H, d, J=6.3 Hz), 1.39-1.77 (2H, m), 2.03 (1H, brm), 3.10 (1H, dt, J=10.4 Hz, J=2.9 Hz), 3.25 (1H, dd, J=7.0 Hz, J=3.1 Hz), 3.51, 4.92 (2H, ABq, J=14.8 Hz), 3.79 (3H, s), 4.13 (1H, dd, J=10.2 Hz, J=3.1 Hz), 4.07-4.26 (1H, m), 5.21, 5.28 (2H, ABq, J=12 Hz), 6.87, 7.39 (4H, A₂B₂q, J=8.8 Hz), 7.05, 8.30 (4H, A₂B₂q, J=6.2 Hz) ppm.

IR (CHCl₃)$\nu$: 3680, 3604, 1772, 1712, 1612, 1586 cm⁻¹.

EXAMPLE B'-12 (silyl in R¹)

R¹=1-(tertbutyldimethylsilyloxy)ethyl, R²=methyl, OR⁶=OH→Cl→SHet, R⁷=p-methoxybenzyl, Het=4-pyridyl Diol (a) (4.28 g; 9.0 millimoles) is esterified with diphenyl chlorophosphate (3.1 ml), triethylamine (2.1 ml; 1.1 equivalents) and dimethylaminopyridine (550 mg; 0.3 equivalents) in dimethylformamide and dichloromethane (10 ml) at −70° C. for 1 hour as in Example B-12 to give a solution of diphenyl phosphate (a). This (a) is treated with 4-mercaptopyridine (1.2 equivalents), triethylamine (1.1 equivalents), sodium iodide (1.2 equivalents), and dimethylformamide at room temperature for 2 hours as in Example F-6 to give starting 4-pyridylsulfide (b) (4.4 g) in 85% yield.

This silylate (b) (2.1 g; 3.69 millimoles) is dissolved in tetrahydrofuran (10 ml), mixed with acetic acid (0.8 ml) and tetrabutylammonium fluoride trihydrate (2.78 g; 2.4 equivalents) and kept at room temperature two nights. The reaction mixture is poured into aqueous sodium hydrogen carbonate-ethyl acetate. The organic layer is separated, washed with water, dried, and concentrated in vacuum, and purified by chromatography (Lober B, ethyl acetate) to give 6α-(1-hydroxyethyl)-1-methyl-2-(4-pyridylthio)methyl-1-carbapen-2-em-3-carboxylic acid p-methoxybenzyl ester (b) (455 mg; Yield: 27.1%; having physical constants as follows from polar fraction) and 6α-(1-hydroxyethyl)-1-methyl-2-(4-pyridylthio)methylidene-1-carbapenam-3-carboxylic acid p-methoxybenzyl ester (100 mg; Yield: 6.0%, from less polar fraction). IR (CHCl$_3$)ν: 3400–3120br, 1750br, 1604, 1575 cm$^{-1}$.

NMR (EM-390, CDCl$_3$)δ: 1.11 (3H, d, J=7.5 Hz), 1.35 (3H, d, J=6.3 Hz), 3.05–3.40 (ca. 3H, m), 4.02 (1H, dd, J=6.3 Hz, J=2 Hz), 4.23 (1H, quintet, J=6.3 Hz), 4.98 (1H, brs), 5.09, 5.24 (2H, ABq, J=11.3 Hz), 6.33 (1H, brs), 6.81, 7.28 (4H, ABq, J=8.4 Hz), 6.91, 8.35 (4H, ABq, J=5.5 Hz) ppm.

[REACTION C: OZONE FISSION]

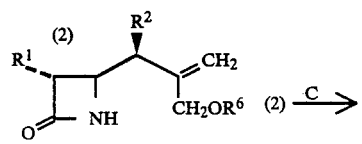

EXAMPLE C-1

R$^1$ = 1-(tert-butyldimethylsilyloxy)ethyl, R$^2$=methyl, R$^6$=trityl

To a solution of methylene (2) (20.7 g) in a mixture of dichloromethane (120 ml) and methanol (30 ml) under dry ice-acetone cooling is introduced ozone until the mixture becomes blue. The ozone inlet is stopped. The mixture is let stand for 30 minutes, freed from excess ozone with nitrogen, mixed with dimethyl sulfide (10 ml), kept at room temperature for 1 hour, and concentrated. The residue is chromatographed over silica gel (110 g). The part eluting with toluene-ethyl acetate (9:1) gives ketone (3) as crystals (14.6 g) on treating with n-hexane. mp. 133°–134° C. (from acetone-hexane). Total yield: 52% from acetate (I).

IR (Nujol)ν: 3240, 3080, 1765, 1727, 1716 cm$^{-1}$.
[α]$_D^{23}$ 0° (c, 1,000 in CHCl$_3$).
[α]$_{365}^{23}$ −18.5° (c, 1.000 in CHCl$_3$).
Elemental analysis: (C$_{34}$H$_{43}$NO$_4$Si) Calcd.: C, 73.21; H, 7.77; N, 2.51. Found: C, 73.20; H, 7.08; N, 2.50.
NMR (VXR200, CDCl$_3$)δ: 0.04 & 0.06 (ca. 6H, 2×s), 0.86 (9H, s), 1.09 (3H, d, J=7.1 Hz), 1.15 (3H, d, J=6.7 Hz), 2.83 (1H, dd, J=4.9 Hz, J=2.2 Hz), 3.15 (1H, dq, J=7.1 Hz, J=4.6 Hz), 3.79 (1H, dd, J=4.6 Hz, J=2.2 Hz), 3.85 (2H, s), 4.05~4.18 (1H, m), 5.81 (1H, brs), 7.25–7.45 (ca. 15H, m) ppm.

EXAMPLE C-2

R$^1$ = 1-(tert-butyldimethylsilyloxy)ethyl, R$^2$=methyl, R$^6$=H

In a similar manner to that of above, ozone is introduced to a solution of methylene (2) in dichloromethane-methanol until the reaction mixture becomes blue. The reaction mixture is worked up as above and the residue is purified by silica gel chromatography to give ketol (3). mp. 89°–91° C. (from acetone-n-hexane).

Elemental analysis: (C$_{15}$H$_{29}$NO$_4$Si) Calcd.: C, 57.11; H, 9.27; N, 4.44. Found: C, 57.13; H, 8.96; N, 4.55.
IR (Nujol)ν: 3452, 3172, 1762, 1733, 1725 cm$^{-1}$.
[α]$_D^{24}$ −36.0°±0.8° (c, 1.012 in CHCl$_3$).
NMR (EM390, CDCl$_3$)δ: 0.07 (ca. 6H, s), 0.85 (ca. 9H, s), 1.14 (3H, d, J=6 Hz), 1.15 (3H, J=7.2 Hz), 2.83 (1H, m), 2.86 (1H, dd, J=4.8 Hz, J=1.7 Hz), 3.42 (1H, brs), 3.77 (1H, dd, J=5.2 Hz, J=1.7 Hz), 4.10 (1H, qd, J=6.0, J=4.8 Hz), 6.72 (1H, brs) ppm.

EXAMPLE C-3

R$^1$ = 1-(tert-butyldimethylsilyloxy)ethyl, R$^2$=ethyl, R$^6$=trityl.

A similar cleavage of methylene (2) (5.00 g) with ozone at −70° C. followed by dimethyl sulfide treatment gives ketol (3) (4.00 g).

Yield: ca. 80%. mp. 153°–155° C. (from n-hexane).
IR (Nujol)ν: 3400, 1760, 1740sh, 1680 cm$^{-1}$.
NMR (EM390, CDCl$_3$)δ: 0.85 (9H, s), 0.80–1.01 (3H, m), 1.04 (3H, d, J=6.5 Hz), 1.33–1.90 (2H, m), 2.81 (1H, dd, J=4.5 Hz, J=1.8 Hz), 2.94–3.17 (1H, m), 3.70 (1H, dd, J=6.0 Hz), 3.76 (2H, s), 4.07 (1H, quintet type), 6.00 (1H, brs), 7.19–7.53 (15H, m) ppm.

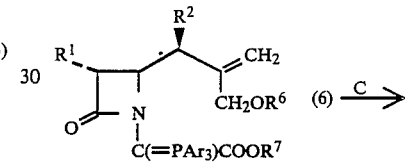

EXAMPLE C-4

R$^1$ = 1-(tert-butyldimethylsilyloxy)ethyl, R$^2$=methyl, R$^6$=trityl, R$^7$=p-methoxybenzyl, Ar=-phenyl.

To a solution of methylene (6) (110 mg; 0.11 millimoles) in dry dichloromethane-methanol (10:1; 3.3 ml) at −70° C. under nitrogen are added trifluoroacetic acid (70 μl; 8 equivalents) and ozone for 10 minutes and then kept standing for 30 minutes. This mixture is mixed with dimethyl sulfide (0.15 ml), stirred at −70° C. for 1 hour, and poured into aqueous diluted sodium bicarbonate. The organic layer is taken, washed with water, dried, concentrated in vacuum, and purified by chromatography on silica gel to give ylidoketone (4) (108 mg). Yield: 93%. mp. 178°–179.5° C. (from ether). This is identical with a product prepared from condensing trityloxyacetone and 4-acetoxy-3-(1-tert-butyldimethylsilyloxyethyl)-2-azetidinone.

EXAMPLE C-5

R$^1$ = 1-hydroxyethyl, R$^2$=methyl, R$^6$=H, R$^7$=p-methoxybenzyl, Ar=phenyl.

To a solution of methylene (6) (150 mg; 0.23 millimoles) in dichloromethane-methanol (10:1; 3 ml) at −78° C. are introduced trifluoroacetic acid (92 μl; 5 equivalents) and ozone over 15 minutes. After keeping for 30 minutes, the mixture is mixed with dimethyl sulfide (0.1 ml), stirred for 30 minutes, and poured onto aqueous sodium hydrogen carbonate. The organic layer is taken, dried, and concentrated in vacuum. The residue is chromatographed over silica gel (15 g; toluene-acetic acid=1:1) to give ketone (4) as powder (72 mg). Yield: 49%.

IR (CHCl$_3$)$\nu$: 3460br, 1740, 1716(sh), 1602sh cm$^{-1}$.

NMR (VXR200, CDCl$_3$)δ: 0.96 (3H, brd, J=6.2 Hz), 1.22 (3H, brd, J=6.8 Hz), 3.74 (3H, s), 3.83 (3H, s), 6.57, 6.58 (3H, 2×s), 6.91 (1H, d, J=8.8 Hz), 7.26–7.80 (17H, m) ppm.

[Reaction D: Glyoxylate adduct→ylide]

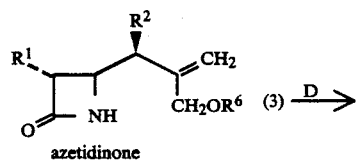
azetidinone

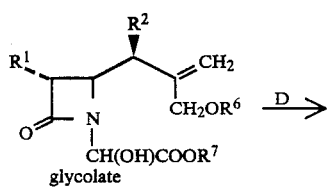
glycolate

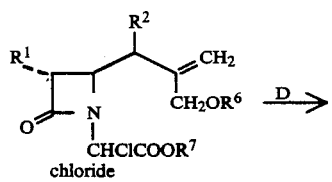
chloride

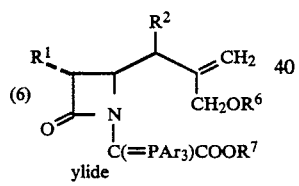
(6) ylide

EXAMPLE D-1

R$^1$=1-(tert-butyldimethylsilyloxy)ethyl, R$^2$=methyl, R$^6$=trityl, R$^7$=p-methoxybenzyl, Ar=-phenyl.

(1) To a solution of azetidinone (2) (1.79 g; 3.22 millimoles) and glyoxylic acid p-methoxybenzyl ester monohydrate (820 mg; 1.2 equivalents) in tetrahydrofuran (6 ml) is added triethylamine (0.22 ml; 0.5 equivalents). After keepting at room temperature overnight, the reaction mixture is poured into water-ethyl acetate mixture and extracted. The ethyl acetate extract is washed with cold hydrochloric acid, aqueous sodium hydrogen carbonate and saline, dried, and concentrated in vacuum. The resulting residue is purified by chromatography over silica gel (24 g) using toluene-ethyl acetate mixture for eluting to give the corresponding adduct glycolate (2.17 g). Yield: 82.5%.

IR (CHCl$_3$)$\nu$: 1740, 1710, 1604 cm$^{-1}$.

(2) To a stirring solution of adduct glycolate in tetrahydrofuran (12 ml) cooling at −40° C. are dropwise added 2,6-lutidine (1.6 ml; 4 equivalents) and thionyl chloride (0.29 ml; 1.2 equivalents). The stirring is continued for a further hour to give a solution of the corresponding chloride.

(3) To the solution of chloride are added triphenyl-phos-phine (845 mg; 3 equivalents), sodium bromide (332 mg; 1 equival-ents) and dioxane (12 ml). After stirring overnight at room temperature, the reaction mixture is poured into ice water-ethyl acetate mixture and extracted. The extract is washed with diluted hydrochloric acid, diluted aqueous sodium hydrogen carbonate, and saline, dried (MgSO$_4$), and concentrated in vacuum. The resulting residue is purified by chromatography over silica gel to give ylide (6) (1.58 g). Yield: 49.4%. mp. 171.5°–173° C. (from ether-petroleum ether).

[α]$_D^{23}$ −22.0°±1.2° (c, 0.509 in CHCl$_3$).

IR (Nujol)$\nu$: 1740, 1622, 1512, 1248 cm$^{-1}$.

Elemental analysis: Calcd.: C, 76.10; H, 6.89; N, 1.41; P, 3.12. (C$_{63}$H$_{68}$NO$_6$PSi) Found: C, 76.19; H, 6.99; N, 1.40; P, 3.38.

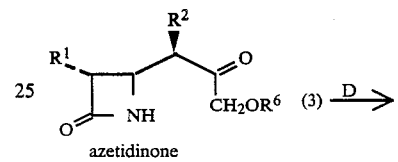
azetidinone

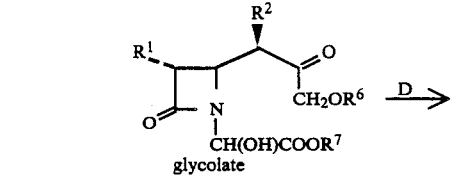
glycolate

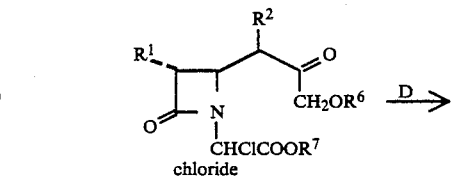
chloride

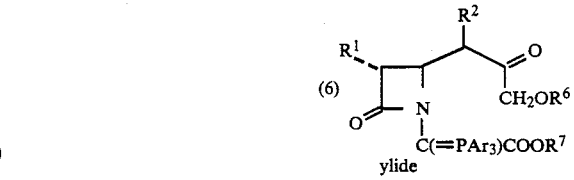
(6) ylide

EXAMPLE D-2

R$^1$=1-(tert-butyldimethylsilyloxy)ethyl, R$^2$=methyl, R$^6$=trityl, R$^7$=p-methoxybenzyl, Ar=-phenyl.

(1) To a solution of azetidinone (3) (7.8 g; 13.98 millimoles) in tetrahydrofuran (24 ml) are added glyoxylic acid p-methoxybenzyl ester monohydrate (3.85 g; 1.3 equivalents) and triethylamine (1 ml; 0.5 equivalents). After stirring at room temperature for 4 hours, the reaction mixture is poured into cold 2N-hydrochloric acid-ethyl acetate mixture and extracted. The extract solution is washed with aqueous sodium hydrogen sulfite, aqueous sodium hydrogen carbonate and water, dried, and concentrated in vacuum to give the corresponding glycolate as foamy residue.

(2) To a solution of the adduct glycolate in tetrahydrofuran (50 ml) at −70° C. are dropwise added 2,6-lutidine (7 ml; 4 equivalents) and thionyl chloride (1.3 ml; 1.28 equivalents). After stirring for 40 minutes, the reaction mixture is washed, dried, and concentrated in vacuum to give the crude corresponding chloride.

(3) To a solution of this chloride in dioxane (50 ml) are added triphenylphosphine (11.1 g; 3 equivalents) and sodium bromide (1.5 g; 1 equivalents). After stirring for 17 hours, the reaction mixture is poured into cold 2N-hydrochloric acid-ethyl acetate and extracted. The extract solution is washed with aqueous sodium hydrogen carbonate and water, dried, and concentr-ated in vacuum. The crystalline residue is crystallized from ether to give ylide (4) (10.4 g). Yield: 74.8%. mp. 178°–179.5° C. (from ether).

$[\alpha]_D^{23}$ −39.6°±0.8° (c, 1.014 in $CHCl_3$).

IR (Nujol)$\nu$: 3064, 1742, 1740, 1621, 1512, 1245 $cm^{-1}$.

Elemental analysis: ($C_{62}H_{66}NO_7PSi$) Calcd.: C, 74.75; H, 6.68; N, 1.41; P, 3.11. Found: C, 74.51; H, 6.70; N, 1.44; P, 3.40.

EXAMPLE D-3

$R^1$ = 1-(tert-butyldimethylsilyloxy)ethyl, $R^2$ = ethyl, $R^6$ = trityl, $R^7$ = p-methoxybenzyl, Ar = phenyl.

(1) In a manner similar to Example D-2, azetidinone derivative (3) (14.7 g; 22.62 millimoles) in tetrahydrofuran (50 ml) is treated with glyoxylic acid p-methoxybenzyl ester (6.5 g; 1.35 equivalents) and triethylamine (1.8 ml; 0.5 equivalents) overnight to give the corresponding glycolate (17.2 g).

(2) This adduct glycolate in tetrahydrofuran (100 ml) at −50° C. is treated with 2,6-lutidine (12.9 g; 4.6 equivalents) and thionyl chloride (2.2 ml; ca. 1.3 equivalents) for 30 minutes to give a solution of the corresponding chloride.

(3) To this solution of the chloride are added triphenylphosphine (29.74 g; 5 equivalents), sodium bromide (2.5 g; 1.1 equivalents) and dioxane (100 ml), and the mixture is stirred for 20 hours. The product is recrystalized from acetone-ethyl acetate-ether mixture to give crystalline ylide (4) (12.84 g).

Yield: 56.2%. mp. 184°–185° C.

IR (Nujol)$\nu$: 1745, 1730, 1621, 1512, 1252 $cm^{-1}$.

$[\alpha]_D^{23}$ −36.8°±0.8° (c, 1.003 in $CHCl_3$).

Elemental analysis: ($C_{63}H_{68}NO_7PSi$) Calcd.: C, 74.90; H, 6.78; N, 1.39; P, 3.07. Found: C, 74.82; H, 6.94; N, 1.42; P, 3.41.

EXAMPLE D-4

$R^1$ = 1-(tert-butyldimethylsilyloxy)ethyl, $R^2$ = methyl, $R^6$ = trityl, $R^7$ = allyl, Ar = phenyl.

(1) To a solution of azetidinone (3) 17.22 g (87 millimoles) in tetrahydrofuran (62 ml) are added glyoxylic acid allyl ester monohydrate (4.9 g; 1.2 equivalents) and triethylamine (2.2 ml; 0.5 equivalents). After keeping at room temperature for 20 hours, the reaction mixture is diluted with ethyl acetate and washed with water. The ethyl acetate layer is taken, washed with saline, dried ($Na_2SO_4$), and concentrated in vacuum to give the corresponding adduct glycolate as residue (18.66 g). Yield: 90%.

(2) To a solution of this adduct glycolate (27.76 millimoles) in tetrahydrofuran (83 ml) cooling at −45° C. are added dropwise 2,6-lutidine (12.7 ml; 4 equivalents) and thionyl chloride (2.6 ml; 1.3 equivalents). After stirring at the same temperature for 30 minutes, the reaction mixture is poured into a mixture of water and ethyl acetate and stirred. The formed ethyl acetate layer is taken, washed with water, and subjected to conventional work up to give the corresponding chloride.

(3) To a solution of this chloride in dioxane (50 ml) are added triphenylphosphine (10.9 g; 1.5 equivalents), 2,6-lutidine (6.4 ml; 2 equivalents) and sodium bromide (4 g). After stirring at room temperature overnight, the reaction mixture is concentrated in vacuum to remove dioxane and the residue is extracted with ethyl acetate. The extract solution is purified by chromatography over silica gel eluting with toluene-ethyl acetate (2:1) to afford ylide (4) (21.8 g). mp. 158°–159° C. (from benzenehexane). Yield: 86%.

Elemental analysis: ($C_{57}H_{62}NO_6PSi$) Calcd.: C, 74.73; H, 6.82; N, 1.53. Found: C, 75.18; H, 6.87; N, 1.62.

IR ($CHCl_3$)$\nu$: 3300–2920, 1730, 1710sh, 1640sh, 1605sh, 1435, 1100 $cm^{-1}$.

[Reaction E: Ring closure]

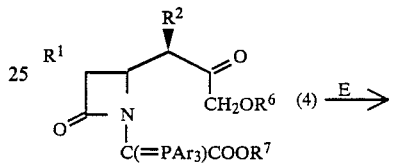

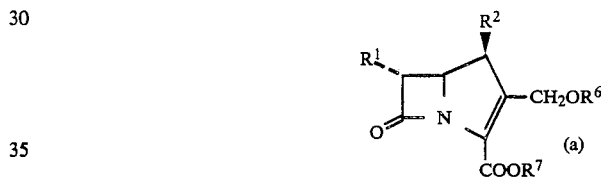

EXAMPLE E-1

$R^1$ = 1-hydroxyethyl, $R^2$ = methyl, $R^6$ = H, $R^7$ = p-methoxybenzyl, Ar = phenyl.

A solution of ylide (4) (13.98 g) in toluene is heated at 110° C. for 1 hour. The reaction mixture is concentrated in vacuum. The residue is dissolved in ethyl acetate, washed with water, dried ($MgSO_4$), and concentrated in vacuum to give 1-carbapen-2-em (a). Yield: 74%.

NMR (VXR-200, $CDCl_3$)$\delta$: 1.19 (3H, d, J = 7.4 Hz), 1.32 (3H, d, J = 6.2 Hz), 1.70–2.70 (2H, brm), 3.15–3.32 (1H, m), 3.26 (1H, dd, J = 2.9 Hz, J = 6.4 Hz), 3.79 (3H, s), 4.17–4.28 (1H, m), 4.18 (1H, dd, J = 10.0 Hz, J = 2.9 Hz), 5.19, 5.26 (2H, ABq, J = 12.2 Hz), 6.88, 7.38 (4H, $A_2B_2$q, J = 8.6 Hz) ppm.

EXAMPLE E-2

$R^1$ = 1-(tert-butyldimethylsilyloxy)ethyl, $R^2$ = methyl, $R^6$ = H, $R^7$ = p-methoxybenzyl, Ar = phenyl.

A solution of ylide (4) in toluene is heated at 100° C. for 1 hour to give 1-carbapen-2-em (a). Yield: 74%.

IR($CCl_4$)$\nu$: 3420br, 1780, 1700, 1616, 1582, 1512, 1244 $cm^{-1}$.

NMR (EM-390, $CDCl_3$)$\delta$: 1.16 (3H, d, J = 7.0 Hz), 1.23 (3H, d, J = 6.2 Hz), 3.0–3.41 (2H, m), 3.20 (1H, dd, J = 3.0 Hz, J = 5.5 Hz), 3.77 (3H, s), 4.12 (1H, dd, J = 6.0 Hz, J = 3.0 Hz), 4.20 (1H, m), 4.40 (2H, t, J = 6 Hz), 5.20 (2H, s), 6.87, 7.37 (4H, $A_2B_2$q, J = 6 Hz) ppm.

EXAMPLE E-3

$R^1$=1-(tert-butyldimethylsilyloxy)ethyl, $R^2$=methyl, $R^6$=trityl, $R^7$=p-methoxybenzyl, Ar=phenyl.

A suspension of ylide (4) (1.08 g; 1.084 millimoles) in toluene (50 ml) is heated at 110° C. After 75 minutes, the mixture is concentrated and the residue is purified by chromatography (Lober B, toluene-ethyl acetate 2:1) to give 1-carbapen-2-em (a) (750 mg) as foam. Yield: 96%.

NMR (EM-390, CDCl$_3$):δ: 0.03 (ca. 6H, s), 0.83 (9H, s), 0.95 (3H, d, J=7.5 Hz), 1.13 (3H, d, J=6.2 Hz), 3.05 (1H, dd, J=5.4 Hz, J=3 Hz), 3.38 (1H, dq, J=10.5 Hz, J=7.5 Hz), 3.69, 4.68 (2H, ABq, J=15 Hz), 3.70 (3H, s), 4.01 (1H, dd, J=10.5 Hz, J=3 Hz), 4.14 (1H, m), 4.97 (2H, s), 6.72 (2H, A$_2$B$_2$, J=9.0 Hz), 7.05-7.40 (17H, m) ppm.

IR (CHCl$_3$)ν: 1770, 1715, 1615, 1588, 1512 cm$^{-1}$.

EXAMPLE E-4

$R^1$=1-hydroxyethyl→1-(triethylsilyloxy)ethyl, $R^2$=methyl, $R^6$=H→acetyl→H, $R^7$=p-methoxybenzyl, Ar=phenyl.

Dihydroxyylide (4) (6.97 g) ($R^1$=1-hydroxyethyl, $R^6$=H: 10.9 millimoles) in dichloromethane at −40° C. is acetylated at $R^6$ with triethylamine (2.3 ml; 1.5 equivalents) and acetyl chloride (1.2 ml; 1.5 equivalents) for 3 hours at room temperature as in Example B-5 to give acetate (4). This is silylated at $R^1$ with triethylsilyl chloride (4.6 ml; 2.5 equivalents) and triethylamine (3.8 ml; 2.5 equivalents) at 0° C. for 3 hours as in Example B-5 to give triethylsilyl acetate (4). This is hydrolyzed in methanol (30 ml) with 5.2N-sodium methylate in methanol (1.2 ml; 0.57 equivalents) for 3 hours at −50° C. as in Example B'-8 to give starting ylide (4).

A solution of this ylide (4) in toluene (300 ml) is heated at 110° C. for 15 minutes and concentrated. The residue is purified by chromatography (Lober B×2, toluene-ethyl acetate=9:1) to give 1-carbapen-2-em (a) (3.7 g). Yield: 71%.

NMR (VXR-200, CDCl$_3$)δ: 0.53-0.65 (6H, m), 0.90-0.99 (9H, m), 1.18 (3H, d, J=7.4 Hz), 1.27 (3H, d, J=6 Hz), 3.10-3.28 (1H, m), 3.22 (1H, dd, J=6.4 Hz, J=3.0 Hz), 3.80 (3H, s), 4.15 (1H, dd, J=10 Hz, J=3 Hz), 4.36, 4.48 (2H, ABqd, J$_{AB}$=12 Hz, J$_{CH2:OH}$=6 Hz), 5.23 (2H, s), 6.89, 7.39 (4H, A$_2$B$_2$q, J=8.8 Hz) ppm.

EXAMPLE E-5

$R^1$=1-(tert-butyldimethylsilyloxy)ethyl, $R^2$=ethyl, $R^6$=H, $R^7$=p-methoxybenzyl, Ar=phenyl.

A solution of ylide (4) (300 mg; 0.39 millimoles) in toluene (30 ml) is heated at 105° C. for 50 minutes and concentrated in vacuum. The residue is purified by chromatography (Lober B, toluene-ethyl acetate=1:1) to give 1-carbapen-2-em (a) (163 mg). Yield: 85.3%.

NMR (VXR-200, CDCl$_3$)δ: 0.02 (ca. 6H, s), 0.80 (9H, s), 0.96 (3H, t, J=7.4 Hz), 1.24 (3H, d, J=6.1 Hz), 1.30-1.73 (2H, m), 2.89 (1H, dt, J=10.6 Hz, J=3.3 Hz), 3.16 (1H, dd, J=6.7 Hz, J=2.9 Hz), 3.25 (1H, m), 3.75 (3H, s), 4.08 (1H, dd, J=10.0 Hz, J=2.9 Hz), 4.14-4.23 (1H, m), 4.30, 7.33 (4H, A$_2$B$_2$q, J=8.8 Hz) ppm.

IR(CHCl$_3$)ν: 3605, 1772, 1700, 1615, 1589, 1515 cm$^{-1}$.

EXAMPLE E-6

$R^1$=1-hydroxyethyl, $R^2$=ethyl, $R^6$=H, $R^7$=p-methoxybenzyl, Ar=phenyl.

A solution of ylide (4) (1.7 g) in toluene (170 ml) is heated at 110° C. for 1.6 hour and concentrated in vacuum. The residue is purified by chromatography over silica gel (Lober B, ethyl acetate-acetonitrile=1:1) to give 1-carbapen-2-em (a) (820 mg). Yield: 84.1%.

IR(CHCl$_3$)ν: 3608, 1775, 1702, 1615, 1590, 1515 cm$^{-1}$.

NMR (VXR-200, CDCl$_3$)δ: 1.01 (3H, t, J=7.3 Hz), 1.36 (3H, d, J=6.3 Hz), 1.31-1.80 (4H, m), 1.9-2.2 (1H, brm), 2.99 (1H, dt, J=11 Hz, J=3.3 Hz), 3.26 (1H, dd, J=6.8 Hz, J=3.0 Hz), 3.79 (3H, s), 4.20 (1H, dd, J=12 Hz, J=3 Hz), 4.13-4.24 (1H, m), 4.35, 4.46 (2H, ABq, J=14 Hz), 6.88, 7.38 (4H, A$_2$B$_2$q, J=8.8 Hz) ppm.

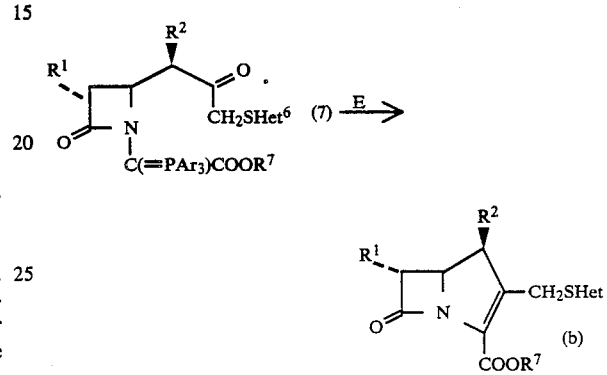

EXAMPLE E-7

$R^1$=1-(triethylsilyloxy)ethyl, $R^2$=ethyl, $R^7$=p-methoxybenzyl, Ar=phenyl, Het=4-pyridyl.

A solution of ylide (7) (1.35 g; 1.56 millimoles) in toluene (140 ml) is heated at 108° C. for 1 hour. The reaction mixture is concentrated in vacuum. The residue is purified by chromatography over silica gel (Lober B, toluene-ethyl acetate 1:1) to give amorphous 1-carbapen-2-em (b) (602 mg). Yield: 66.2%.

NMR (VXR-200, CDCl$_3$)δ: 0.61 (9H, t, J=7.6 Hz), 0.86-1.02 (9H, m), 1.31 (3H, d, J=5.9 Hz), 1.35-1.85 (4H, m), 3.06-3.15 (1H, td-type), 3.22 (1H, dd, J=7.0 Hz, J=3.1 Hz), 3.54 and 4.94 (2H, ABq, J=14 Hz), 3.82 (3H, s), 4.08 (1H, dd, J=10.2 Hz, J=3.1 Hz), 4.15-4.28 (1H, quintet-type), 6.89, 7.40 (4H, A$_2$B$_2$q, J=8.3 Hz), 7.09, 8.35 (4H, A$_2$B$_2$q, J=5.1 Hz) ppm.

IR (CCl$_4$)ν: 1780, 1713, 1614, 1572, 1247 cm$^{-1}$.

EXAMPLE E-8

$R^1$=1-hydroxyethyl, $R^2$=ethyl, $R^6$=H, $R^7$=p-methoxybenzyl, Ar=phenyl, Het=4-pyridyl.

Ketol (4) (600 mg; ca. 0.81 millimoles) in dichloromethane (4 ml) under nitrogen are dropwise added methanesulfonyl chloride (0.08 ml; ca. 1.3 equivalents) and triethylamine (0.3 ml; 2.6 equivalents) at −50° C. for 30 minutes as in Example B-7 to give the corresponding mesylate as $R^6$ (4). The mesylate is treated with 4-mercaptopyridine (129 mg; 1.4 equivalents) in acetonitrile (2 ml) under ice cooling for 1 hour as in Example F-3 to give starting pyridylsulfide (7) as foamy residue.

A solution of this pyridylsulfide (7) in toluene (35 ml) is heated at 110° C. for 1 hour. The reaction mixture is concentrated in vacuum. The residue is purified by chromatography (Lober B, ethyl acetate-acetonitrile-dichloromethane-hexane=1:1:1) to give 6α-(1-hydroxyethyl)-1-ethyl-2-(4-pyridylthio)methylidene-1-carbapenam-3-carboxylic acid p-methoxybenzyl ester (75 mg; IR (CHCl$_3$)ν: 3400–3150br, 1750, 1604, 1575 cm$^{-1}$, Yield: 19.8%) from the first fraction, followed by 6α-(1-hydroxyethyl)-1-ethyl-2-(4-pyridylthio)methyl-1-carbapen-2-em-3-carboxylic acid p-methoxybenzyl ester (b) {86 mg; IR (CHCl$_3$)ν: 3680, 3604, 1772, 1712, 1612, 1586 cm$^{-1}$, Yield: 22.8%} and 6α-(1-(4-pyridylthio)ethyl)-1-ethyl-2-(4-pyridylthio)methyl-1-carbapen-2-em-3-carboxylic acid p-methoxybenzyl ester {128 mg; NMR (EM-390, CDCl$_3$)δ: 0.97 (3H, t, J=7 Hz), 1.30, 1.33 (3H, 2×d, J=6 Hz), 1.45–1.80 (2H, m), 3.17 (1H, dt, J=3 Hz, J=9 Hz), 3.53, 4.88 (2H, ABq, J=14 Hz), 3.76 (3H, s), 3.93–4.26 (3H, m), 5.25 (2H, s), 6.83 (2H, d, J=6 Hz), 7.0–8.40 (ca. 10H, m) ppm}.

EXAMPLE E-9

R$^1$=1-hydroxyethyl, R$^2$=ethyl, R$^7$=p-methoxybenzyl, Ar=phenyl.

A solution of ylide (7) (2.10 g; 2.81 millimoles) in toluene (200 ml) is heated at 110° C. for 70 minutes and concentrated in vacuum. The residue is purified by chromatography to give 1-carbapen-2-em (b) (975 mg). Yield: 73.9%.

NMR (VXR-200, CDCl$_3$)δ: 1.04 (3H, t, J=7.4 Hz), 1.35 (3H, d, J=6.3 Hz), 1.39–1.77 (2H, m), 2.03 (1H, brm), 3.10 (1H, dt, J=10.4 Hz, J=2.9 Hz), 3.25 (1H, dd, J=7.0 Hz, J=3.1 Hz), 3.51, 4.92 (2H, ABq, J=14.8 Hz), 3.79 (3H, s), 4.13 (1H, dd, J=10.2 Hz, J=3.1 Hz), 4.07–4.26 (1H, m), 5.21, 5.28 (2H, ABq, J=12 Hz), 6.87, 7.39 (4H, A$_2$B$_2$q, J=8.8 Hz), 7.05, 8.30 (4H, A$_2$B$_2$q, J=6.2 Hz) ppm.

IR (CHCl$_3$)ν: 3680, 3604, 1772, 1712, 1612, 1586 cm$^{-1}$.

EXAMPLE E-10

R$^1$=1-hydroxyethyl, R$^2$=methyl, R$^7$=allyl, Ar=-phenyl, Het=4-pyridyl.

A solution of ylide (7) (1.7 g; 2.6 millimoles) in benzene (180 ml) is refluxed for 4 hours and concentrated in vacuum. The residue is purified by chromatography {toluene:ethyl acetate (1:1) and hexane:dichloromethane:ethyl acetate:acetonitrile (1:1:1:1)} over silica gel to give 1-carbapen-2-em (b) (0.75 g). Yield: 77%.

IR (CHCl$_3$)ν: 3600–3100, 2965, 1770, 1712, 1575, 1285 cm$^{-1}$.

UV (CH$_3$CN)μ: 254, 278 nm.

NMR (VXR200, CDCl$_3$)δ: 1.18 (3H, d, J=7 Hz), 1.31 (3H, d, J=6.3 Hz), 3.26 (1H, dd, J=3.1 Hz, J=6.6 Hz), 3.35 (1H, m), 3.53, 4.99 (2H, ABq, J=14.3 Hz), 4.19 (2H, m), 4.77 (2H, m), 5.25–5.05 and 5.85–6.10 (3H, 2×m), 7.14, 8.37 (4H, A$_2$B$_2$q, J=6.4 Hz) ppm.

[Reaction F: Introduction of nucleophilic group]

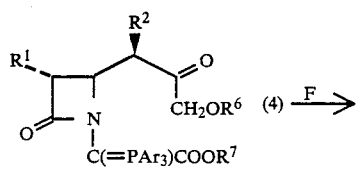

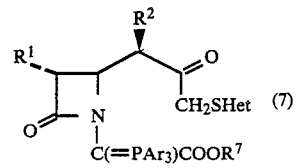

EXAMPLE F-1

R$^1$=1-(triethylsilyloxy)ethyl→1-hydroxyethyl,
R$^2$=ethyl, OR$^6$=OH→O-mesyl→SHet,
R$^7$=p-methoxybenzyl, Ar=phenyl, Het=4-pyridyl.

Alcohol (4) (4.41 g; 5.74 millimoles) is treated with methanesulfonyl chloride (0.49 ml; 1.1 equivalents) and triethylamine (1.84 ml; 2.3 equivalents) in dichloromethane (22 ml) at −60° C. for 1 hour as in Example B-6 to give starting mesylate (4).

This solution of resulting mesylate (4) is mixed with 4-mercaptopyridine (803 mg; 1.25 equivalents) and acetonitrile (22 ml), warmed to room temperature, and stirred for 2 hours to give a solution of pyridylsulfide (7).

This product (7) is treated with concentrated hydrochloric acid (3.2 ml; 6.5 equivalents) and acetic acid (6 ml) at 0° C. for 2 hours as in Example B'-10 to give alcohol (7) (3.52 g). Yield: 82%. IR (CHCl$_3$)ν: 3620–3300, 1745, 1720sh, 1619, 1582 cm$^{-1}$.

EXAMPLE F-2

R$^1$=1-hydroxyethyl, R$^2$=methyl, OR$^6$=OH→Cl, R$^7$=allyl, Ar=phenyl, Het=4-pyridyl.

Diol (4) (9.52 g; 17 millimoles) in acetonitrile (85 ml) and carbon tetrachloride (34 ml) is treated with triphenylphosphine (5.4 g; 1.2 equivalents) under ice cooling for 2 hours as in Example B-8 to give a solution of starting chloride (4).

This solution of chloride (4) is mixed with 4-mercaptopyridine (2.45 g; 1.3 equivalents) and sodium carbonate (1.8 g; 1 equivalents) and concentrated in vacuum. The residue is dissolved in toluene, filtered to remove solid, and extracted with toluene. This is extracted with 2N-hydrochloric acid, mixed with sodium hydrogen carbonate, reextracted with toluene, and worked up as usual to give 4-pyridylsulfide (7) (7.87 g). Yield: 71%. IR (CHCl$_3$)ν: 3100–2900, 1735, 1707, 1610, 1430 cm$^{-1}$.

EXAMPLE F-3 (4-PYRIDYLTHIO)

R$^1$=1-hydroxyethyl, R$^2$=ethyl, R$^6$=H, R$^7$=p-methoxybenzyl, Het=4-pyridyl.

Diol (4) (600 mg; ca. 0.81 millimoles) is treated with methanesulfonyl chloride (0.08 ml; ca. 1.3 equivalents) and triethylamine (0.3 ml; 2.6 equivalents) in dichloromethane (4 ml) at −50° C. for 30 minutes under nitrogen as in Example B-7 to give starting mesylate (4).

To the resulting solution of mesylate (4) is added 4-mercaptopyridine (129 mg; 1.4 equivalents) and acetonitrile (2 ml) and stirred under ice cooling for 1 hour. The reaction mixture is poured into ice-water and adjusted at pH 6.0. The organic layer is separated, washed with aqueous sodium hydrogen carbonate and water, dried, and concentrated in vacuum to give pyridyl sulfide (7) as foamy residue.

This product (7) in toluene (35 ml) is heated at 110° C. for 1 hour as in Example E-8 to give 6α-(1-hydroxyethyl)-1-ethyl-2-(4-pyridylthio)methylidene-1-carbapenam-3-carboxylic acid p-methoxybenzyl ester (75 mg), 6α-(1-hydroxyethyl)-1-ethyl-2-(4-pyridylthio)methyl-1-carbapen-2-em-3-carboxylic acid p-methoxybenzyl ester (b) (86 mg), and 6α-(1-(4-pyridylthio)ethyl)-1-ethyl-2-(4-pyridylthio)methyl-1-carbapen-2-em-3-carboxylic acid p-methoxybenzyl ester (128 mg).

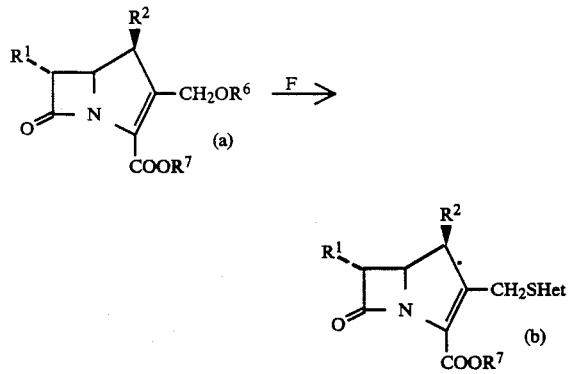

EXAMPLE F-4

$R^1$=1-(triethylsilyloxy)ethyl, $R^2$=methyl, $OR^6$=OH→Cl→SHet, $R^7$=p-methoxybenzyl, Het=4-pyridyl.

Alcohol (a) (800 mg; 1.68 millimoles) is esterified with diphenyl chlorophosphate (0.42 ml; 1.2 equivalents), 4-(dimethylamino)pyridine (40 mg; 0.2 equivalents), and triethylamine (0.28 ml; 1.2 equivalents) in dichloromethane (10 ml) at −60° C. for 30 minutes and recovered its silyl with triethylsilyl chloride (0.75 ml; 3.9 equivalents) for 1 hour as in Example B-10 to give starting 2-chloride of (a).

To a solution of this 2-chloride of (a) in acetonitrile (10 ml) are added 4-mercaptopyridine (280 mg; 1.5 equivalents) and triethylamine (0.35 ml; 1.5 equivalents). After 1 hour at −20° C., the reaction mixture is diluted with dichloromethane and poured into aqueous sodium hydrogen carbonate. The organic layer is separated, washed with aqueous ammonium chloride and water, dried (MgSO4), and concentrated in vacuum. The residue is purified by chromatography over silica gel (60 g) using toluene-ethyl acetate (1:2) to give 4-pyridyl sulfide (b) (680 mg). Yield: 71.6%.

NMR (EM-390, CDCl3)δ: 0.52–0.68 (6H, m), 0.85–1.00 (9H, m), 1.15 (3H, d, J=8.7 Hz), 1.23 (3H, d, J=6 Hz), 3.18 (1H, dd, J=6.0 Hz, J=2.2 Hz), 3.09–3.30 (1H, m), 3.46, 4.91 (2H, ABq, J=14.4 Hz), 3.78 (3H s), 4.09 (1H, dd, J=13 Hz, J=2.2 Hz), 4.3–4.1 (1H, m), 5.21 (2H, s), 6.85, 7.30 (4H, ABq, J=9 Hz), 7.06, 8.30 (4H, ABq, J=6 Hz) ppm.

EXAMPLE F-5

$R^1$=1-hydroxyethyl, $R^2$=methyl, $OR^6$=OH→OPO(OPh)2→SHet, $R^7$=p-methoxybenzyl, Het=4-pyridyl.

Diol (a) (5.42 g; 15.0 millimoles) in dichloromethane (30 ml) is treated with dimethylaminopyridine (550 mg; 0.3 equivalents), diphenyl chlorophosphate (3.1 ml), and triethylamine (2.1 ml; 1.1 equivalents) for 75 minutes at −70° C. as in Example B-11 to give a solution of starting diphenyl phosphate (a).

This solution is mixed with 4-mercaptopyridine (2.00 g; 1.2 equivalents), triethylamine (2.1 ml; 1.1 equivalents), sodium iodide (2.7 g; 1.2 equivalents), and dimethylformamide (30 ml), warmed up to room temperature, and stirred for 2 hours. The mixture is poured onto aqueous sodium hydrogen carbonate-ethyl acetate. The organic layer is separated, washed with water, dried, and concentrated in vacuum. The residue is chromatographed over Lober B eluting with ethyl acetate to give 4-pyridyl sulfide (b) (2.30 g). Yield: 33.7%.

IR (CHCl3)ν: 3370–3130br, 1766, 1708, 1614, 1580 cm⁻¹.

NMR (VXR-200, CDCl3)δ: 1.18 (3H, d, J=7.2 Hz), 1.32 (3H, d, J=6.4 Hz), 1.76 (>1H, brs), 3.25 (1H, dd, J=6.5 Hz), J=3.0 Hz), 3.30–3.39 (1H, m), 3.48 (1H, ABq, J=14.4 Hz), 3.80 (3H, s), 4.13 (1H, dd, J=10.2 Hz, J=3 Hz), 4.22 (1H, t-type, J=6.3 Hz), 4.94 (1H, ABq, J=14.4 Hz), 5.22, 5.28 (2H, d, J=11.8 Hz), 6.88, 7.39 (4H, A2B2q, J=8.8 Hz), 7.06, 8.31 (4H, dA2B2 q, J=4.6 J=1.6 Hz) ppm.

EXAMPLE F-6

$R^1$=1-(tert-butyldimethylsilyloxy)ethyl, $R^2$=methyl, $OR^6$=OH→OPO(OPh)2→SHet, $R^7$=p-methoxybenzyl, Het=4-pyridyl.

Diol (a) (4.28 g; 9.0 millimoles) is treated with dimethylaminopyridine (550 mg; 0.3 equivalents), triethylamine (2.1 ml; 1.1 equivalents), and diphenyl chlorophosphate (3.1 ml) in dimethylformamide and dichloromethane (10 ml) at −70° C. for about 1 hour as in Example B-12 to give a solution of starting diphenyl phosphate (a).

To this solution of ester (a) are added 4-mercaptopyridine (1.2 equivalents), triethylamine (1.1 equivalents), sodium iodide (1.2 equivalents) and dimethylformamide. The mixture is warmed to room temperature, stirred for 2 hours, and poured into aqueous sodium hydrogen carbonate-ethyl acetate. The organic layer is separated, washed with water, dried, and concentrated in vacuum. The residue is purified by chromatography over silica gel (Lober B, ethyl acetate) to give 4-pyridyl sulfide (b) (4.4 g). Yield: 85%.

This product (b) (2.1 g; 3.69 millimoles) is dissolved in tetrahydrofuran (10 ml), mixed with acetic acid (0.8 ml) and tetrabutylammonium fluoride trihydrate (2.78 g; 2.4 equivalents) and kept at room temperature for two nights as in Example B'-12 to give 6α-(1-hydroxyethyl)-1-methyl-2-(4-pyridylthio)methylidene-1-carbapenam-3-carboxylic acid p-methoxybenzyl ester (100 mg; Yield: 6.0%, from less polar fraction) and 6α-(1-hydroxyethyl)-1-methyl-2-(4-pyridylthio)methyl-1-carbapen-2-em-3-carboxylic acid p-methoxybenzyl ester (b) (455 mg; Yield: 27.1%; having physical constants as follows from polar fraction).

IR (CHCl3)ν: 3400–3120br, 1750br, 1604, 1575 cm⁻¹.

EXAMPLE F-7

$R^1$=1-(triethylsilyloxy)ethyl, $R^2$=methyl, $OR^6$=OH→SHet, $R^7$=p-methoxybenzyl, Het=3-pyridyl.

To a solution of alcohol (a) (2.45 g; 5.15 millimoles) and 3-mercaptopyridine disulfide (1.36 g; 1.2 equivalents) in dichloromethane at −30° C. are added tributylphosphine (1.5 ml; 1.2 equivalents) with stirring for 2 hours and then ethanol (0.15 ml) with stirring for 15 minutes. The mixture is poured into ice water. The organic layer is separated and concentrated in vacuum. The residue is purified by chromatography (Lober B×2, toluene-ethyl acetate=4:1) to give 3-pyridyl sulfide (b) (1.86 g). Yield: 64%.

NMR (VXR-200, CDCl3)δ: 0.53–0.64 (6H, m), 0.90–0.98 (9H, m), 1.14 (3H, d, J=7.4 Hz), 1.25 (3H, d,

J=6.2 Hz), 3.19 (1H, dd, J=6.5 Hz, J=3 Hz), 3.24–3.39 (1H, m), 3.36, 4.80 (2H, ABq, J=14 Hz), 3.81 (3H, s), 4.08 (1H, dd, J=10.2 Hz, J=3 Hz), 4.19 (1H, quintet-type, J=6.3 Hz), 5.10 (2H, s), 6.88, 7.34 (4H, A₂B₂q, J=8.8 Hz), 7.09 (1H, dd, J=8.0 Hz, J=4.8 Hz), 7.60 (1H, ddd, J=8.0 OHz, J=2.3 Hz, J=1.7 Hz), 8.42 (1H, dd, J=4.8 Hz, J=15 Hz), 8.57 (1H, d, J=1.7 Hz) ppm.

IR (CHCl₃)ν: 1776, 1717, 1620, 1520 cm⁻¹.

EXAMPLE F-8

$R^1$=1-(triethylsilyloxy)ethyl, $R^2$=methyl, $OR^6$=OH→Cl→SHet, $R^7$=p-methoxybenzyl, Het=2-pyridyl.

In a manner similar to that of Examples F-3 or F-4 for 4-pyridyl sulfide, alcohol (a) is treated with 2-mercaptopyridine or its disulfide to give 2-pyridyl sulfide (b). Yield: 40–60%.

NMR (VXR-200, CDCl₃)δ: 0.51–0.63 (6H, m), 0.88–0.96 (9H, m), 1.17 (3H, d, J=7.4 Hz), 1.24 (3H, d, J=6.2 Hz), 3.14–3.30 (1H, m), 3.20 (1H, dd, J=6.4 Hz, J=3.0 Hz), 3.79 (3H, s), 4.09 (1H, dd, J=10.2 Hz, J=3 Hz), 4.16 (1H, quintet-type, J=6.2 Hz), 4.07, 4.81 (2H, ABq, J=13.8 Hz), 5.24 (2H, s), 6.87, 7.39 (4H, A₂B₂q, J=8.6 Hz), 6.92–7.47 (3H, m), 8.32 (1H, dd-type) ppm.

IR (CHCl₃)ν: 1770, 1712, 1615, 1580 cm⁻¹.

[Reaction G: Carboxy deprotection]

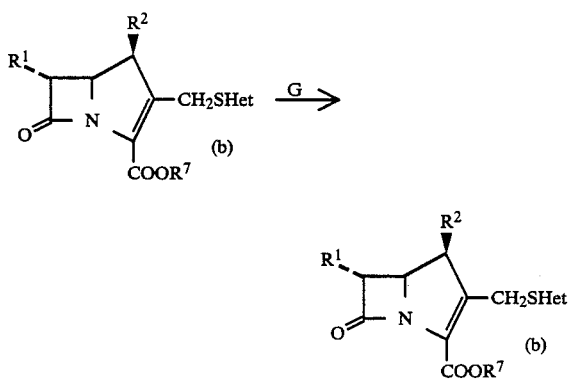

EXAMPLE G-1

$R^1$=1-hydroxyethyl, $R^2$=methyl, $R^7$=p-methoxybenzyl→sodium, Het=4-pyridyl.

To a solution of p-methoxybenzyl ester (b) sulfoxide (90 mg; 0.9 millimoles) in dichloromethane-anisole (4:1; 10 ml) at −45° C. are added aluminum chloride (150 mg; ca. 6 equivalents), and the mixture is stirred for 1 hour. The reaction mixture is mixed with aqueous sodium bicarbonate (284 mg), filtered to remove solid, and chromatographed over HP-20 (ca. 50 ml) to give sodium salt (b) sulfoxide (35 mg). Yield: 49%.

NMR (VXR-200, D₂O-DSS)δ: 1.08 (3H, d, J=6.6 Hz), 1.25, 1.26 (3H, 2×d, J=6.4 Hz), 2.87–3.20 (1H, m), 3.38, 3.40 (ca. 1H, 2×dd, J=6 Hz, J=3 Hz), 3.94–4.24 (ca. 2H, m), 4.15, 4.69 (2H, ABq, J=13.6 Hz), 7.64, 7.69 (2H, 2×d, J=6.2 Hz), 8.72 (2H, brs) ppm.

EXAMPLE G-2

$R^1$=1-hydroxyethyl, $R^2$=ethyl, $R^7$=p-methoxybenzyl→sodium, Het=4-pyridyl.

To a solution of p-methoxybenzyl ester (b) (200 mg; 0.427 millimoles) in dichloromethane (8 ml) and anisole (2 ml) with stirring at −50° C. is added aluminum chloride (270 mg; 4.7 equivalents), and the mixture is stirred for 1 hour. The reaction mixture is diluted with aqueous solution of sodium bicarbonate (615 mg) in water (10 ml), filtered to remove solid, and purified by chromatography over and HP-20 (ca. 30 cc) eluting with aqueous 10% methanol, and lyophilized to give sodium salt (b) (125 mg). Yield: 79%.

Elemental analysis (C₁₇H₁₉N₂O₄SNa.1¼H₂O): Calcd.: C, 51.97; H, 5.52; N, 7.13; S, 8.16; Na, 5.85. Found: C, 51.82; H, 5.44; N, 7.14; S, 7.71; Na, 6.55.

NMR (VXR-200, D₂O, internal reference=DSS)δ: 0.91 (3H, t, J=7 Hz), 1.27 (3H, d, J=6.2 Hz), 1.32–1.82 (2H, m), 3.13 (1H, m), 3.38 (1H, dd, J=6.2 Hz, J=2.6 Hz), 3.63 (1H, ABq-A part, J=14.5 Hz), 4.00 (1H, dd, J=9.5 Hz, J=2.6 Hz), 4.19 (1H, t-type, J=6 Hz), 4.88 (1H, ABq-B part, J=14.5 Hz), 7.31 (2H, A₂B₂q-A part, J=5 Hz), 8.30 (2H, A₂B₂q-B part, J=5 Hz) ppm.

EXAMPLE G-3

$R^1$=1-hydroxyethyl, $R^2$=methyl, $R^7$=allyl→negative charge, Het=1-carbamoyloxymethylpyridinio-4-yl To a solution of allyl ester (b) iodide (560 mg) (1 millimoles) in nitromethane (20 ml)-ethyl acetate (40 ml)-dichloromethane (60 ml) mixture is added triphenylphosphine (262 mg; 1 equivalents), 1M-sodium 2-ethylhexanoate in ethyl acetate (1 ml; 1 equivalents) at 0° C., and strired. At the same temperature, the reaction mixture is mixed with palladium tetrakistriphenylphosphine (120 mg; 0.1 equivalents) and stirred for 1.5 hours. The reaction mixture is diluted with dichloromethane (100 ml) and extracted with water. The water layer is washed with dichloromethane and chromatographed (water, aqueous 20% methanol) over HP20AG column to give inner salt (b) (163 mg). Yield: 42%.

NMR (VXR-200, D₂O, internal standard=DSS)δ: 1.10 (3H, t, J=7.4 Hz) 1.26 (3H, d, J=6.6 Hz), 3.27–3.39 (1H, m), 3.43 (1H, dd, J=6.1 Hz, J=2.9 Hz), 3.89, 5.10 (2H, ABq, J=15.0 Hz), 4.08 (1H, dd, J=10.0 Hz, J=2.6 Hz), 4.13–4.27 (1H, m), 5.30 (2H, s), 7.82, 8.39 (2H, A₂B₂q, J=5 Hz) ppm.

IR (KBr)ν: 3400br, 1750, 1700, 1590 cm⁻¹.

[Reaction H: Additional modifications]

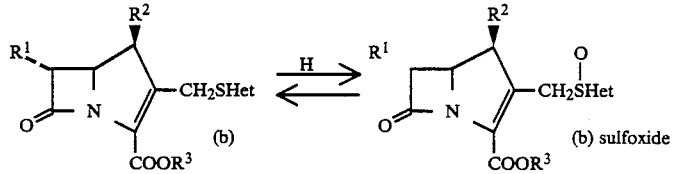

EXAMPLE H-1 (SULFOXIDE FORMATION)

$R^1$=1-hydroxyethyl, $R^2$=methyl, $R^7$=p-methoxybenzyl, Het=4-pyridyl.

To a stirring solution of (ca. 1:1; 1.00 g; 2.2 millimoles) of sulfide (b) and its double bond position isomer, 2-(4-pyridylthio)methylidene-1-carbapenam, in dichloromethane (10 ml) under ice cooling are added sodium hydrogen carbonate (290 mg) and m-chloroperbenzoic acid (710 mg; 70%, 1.3 equivalents). After stirring for 3 hours, the reaction mixture is diluted with water. The dichloromethane layer is separated, washed with sodium hydrogen sulfite and water, dried, and concentrated in vacuum. The residue is purified by chromatography (ethyl acetate:acetonitrile=1:1) over silica gel (20 g) to give the corresponding (b) sulfoxide and its double bond position isomer (370 mg) (ca. 1:1 mixture of the stereoisomers). Total yield: 35.8%.

IR (CHCl$_3$)$\nu$: 1774, 1710, 1616, 1574, 1055 cm$^{-1}$.

NMR (VXR-200, CDCl$_3$)$\delta$: 1.12, 1.17 (3H, 2×d, J=7.4 Hz), 1.30, 1.33 (3H, 2×d, J=5.8 Hz, J=6.2 Hz), 1.80–2.75 (ca. 1H, m), 3.23–3.54 (2H, m), 3.37, 4.59 (ca. 1H, ABq, J=12.4 Hz), 3.80, 3.81 (3H, 2×s), 3.89, 4.50 (ca. 1H, ABq, J=13.4 Hz), 4.10–4.54 (2H, m), 5.03, 5.12 (ca. 1H, ABq, J=12 Hz), 5.17, 5.27 (ca. 1H, ABq, J=12 Hz), 6.90, 6.92 (2H, dd, J=8.8 Hz), 7.33–7.44 (4H, m), 8.64, 8.73 (2H, dd, J=5.8 Hz) ppm.

EXAMPLE H-2 (SULFOXIDE REDUCTION)

This (b) sulfoxides mixture (130 mg; 0.276 millimoles) in acetone (1.3 ml) at −30° C. is mixed with potassium iodide (190 mg; 4 equivalents) and acetyl chloride (0.08 ml; 4 equivalents), and stirred for 1 hour. The reaction mixture is poured into cold aqueous sodium bisulfite and extracted with ethyl acetate. The extract solution is washed with aqueous sodium hydrogen carbonate and water, dried, and concentrated in vacuum. The residue is purified by chromatography (ethyl acetate) over silica gel (5 g) to give (b) sulfide and its double bond position isomer (49 mg). Yield: 39%.

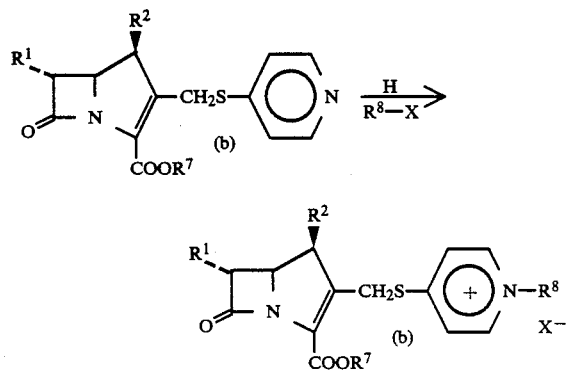

EXAMPLE H-3 (PYRIDINIO FORMATION)

$R^1$=1-hydroxyethyl, $R^2$=ethyl, $R^7$=p-methoxybenzyl, $R^8$=methyl, X=I.

To a solution of pyridylsulfide (b) (345 mg; 0.74 millimoles) in dichloromethane (1 ml) is added methyl iodide (0.23 ml; 5 equivalents), and the mixture is kept at room temperature overnight under nitrogen. Then the separating crystals are collected by filtration, washed with acetone and dried to give 1-methylpyridinio iodide (b) (364 mg). Yield: 81.8%. mp. 139°–140° C. (decomposition).

IR (Nujol)$\nu$: 3516, 3472, 3372, 3120, 1770, 1699, 1630, 1610, 1555, 1519, 1497, 1252, 815 cm$^{-1}$.

Elemental analysis: Calcd.: C, 51.15; H, 5.12; N, 4.59; S, 5.25. (C$_{25}$H$_{28}$N$_2$O$_5$S.CH$_3$I) Found: C, 50.47; H, 5.14; N, 4.61; S, 5.71.

NMR (VXR-200, d$_6$-DMSO)$\delta$: 0.92 (3H, t, J=7.5 Hz), 1.16 (3H, d, J=6.3 Hz), 1.30–1.88 (2H, m), 2.96–3.08 (1H, m), 3.75 (3H, s), 3.91–4.05 (1H, m), 4.10–4.21 (1H, m), 4.18 (3H, s), 4.24, 4.65 (2H, AB q, J=10.5 Hz), 5.13, 5.19 (2H, ABq, J=4.8 Hz), 6.88, 7.35 (4H, A$_2$B$_2$ q, J=8.1 Hz), 7.84, 8.56 (4H, A$_2$B$_2$q, J=6.3 Hz) ppm.

EXAMPLE H-4 (PYRIDINIO FORMATION)

$R^1$=1-hydroxyethyl, $R^2$=methyl, $R^7$=allyl, $R^8$=CH$_2$CONH$_2$, X=I.

To a solution of pyridylsulfide (b) (0.99 g; 2.64 millimoles) in acetonitrile (13 ml) is added iodoacetamide (1.47 g; 3 equivalents), and the mixture is stirred at room temperature for 8 hours. The reaction mixture is diluted with ethyl acetate and resulting precipitate is collected, washed with ethyl acetate, and dried in vacuum to give 1-carbamoylmethyl-4-pyridiniosulfide iodide (b) (1.27 g). Yield: 86%.

IR (CHCl$_3$)$\nu$: 3600–3100, 1735sh, 1728, 1715sh, 1375, 1260–1160 cm$^{-1}$. UV(CH$_3$CN)$\mu$: 246, 307 nm.

Followings are preferable embodiments of this invention:

From the process aspect, 4-(leaving group substituted)azetidin-2-one (I) is reacted with trans-2-(leaving group substituted)methyl-3-alkylacrylic acid (III) and a reducing metal to give 4β-(1β-alkyl-2-carboxyprop-2-enyl)azetidin-2-one (II). The reaction is carried out in a solvent, especially tetrahydrofuran and the reducing metal has the oxido-reduction potential of −0.1 to −0.8 volt and is especially zinc, preferably activated with cupric bromide. The reaction is at −10° to 50° C. for 0.5 to 10 hours especially at 30° to 35° C. for 3.5 hours.

From substance aspect, $R^1$ is hydrogen, 1C to 10C alkyl, 1C to 10C hydroxyalkyl optionally protected by 3C to 18C hydrocarbylsilyl, 1C to 8C haloalkyl, or 4C to 8C dioxolenyl, preferably 1C to 8C alkyl, or 1C to 8C 1-(optionally protected hydroxy or halo)alkyl, where the optional protective group is 1C to 10C carboxylic acyl, 2C to 10C carbonic acyl, 2C to 8C ether forming group, 3C to 18C hydrocarbylsilyl, 7C to 19C reactive aralkyl, and specifically 1-hydroxyethyl, 1-t-butyldimethylsilyloxy)ethyl, or 1-(triethylsilyloxy)ethyl; $R^2$ is 1C to 8C alkyl or substituted alkyl, especially 1C to 3C alkyl or 1C to 5C haloalkyl, specifically methyl or ethyl; $R^3$ is hydrogen or 1C to 8C alkyl, especially hydrogen, methyl, or ethyl; and $R^4$ and $R^5$ each is 1C to 8C optionally substituted alkanoyloxy, 7C to 15C aroyloxy, 1C to 8C alkylsulfonyloxy, 1C to 8C substituted alkylsulfonyloxy, 6C to 10C arylsulfonyloxy, 1C to 8C alkylsulfinyl, 6C to 10C arylsulfinyl, fluoro, chloro, or bromine, specifically $R^4$ acetoxy and $R^5$ is bromine.

From substance aspects in further processing A to H, $R^6$ is hydrogen, 1C to 8C alkanoyl or aroyl, 2C to 10C carbonic acyl 2C to 10C carbonic acyl, 2C to 8C ether forming group, 3C to 18C alkyl, or 7C to 19C reactive aralkyl, especially hydrogen, chlorine, acetyl, methanesulfonyl, trityl, or tert-butyldimethylsilyl; $R^7$ is hydrogen or a 1C to 19C carboxy protective group, especially hydrogen, 1C to 8C alkyl, 3C to 8C alkenyl 7C to 19C aralkyl, 6C to 12C aryl, 1C to 12C amino, 3C to 12C alkylsilyl, 3C to 12C alkylstannyl, lithium, sodium, potassium, magnesium, or calcium, specifically hydrogen, allyl, p-methoxybenzyl, or sodium: Het is optionally substituted 5 or 6 membered (mono or di)cyclic heterocyclic aryl having oxygen, nitrogen, and/or sulfur as hetero atoms, especially furyl, thienyl, pyrrolyl, oxazolyl, thiazolyl, imidazolyl, oxadiazolyl, thiadiazolyl, triazolyl, thiatriazolyl, tetrazolyl, pyridyl, indolyl, benzoimidazolyl, benzothiazolyl, or quinolyl, specifically pyridyl, 1-methylpyridinio-4-yl, or 1-carbamoylmethylpyridinio-4-yl.

What is claimed is:

1. A process for the preparation of a 4β-(1β-alkyl-2-carboxyprop-2-enyl) azetidin-2-one of the formula

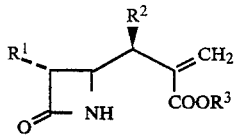 (II)

which comprises reacting a 4-(leaving group substituted) azetidin-2-one of the formula

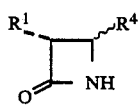 (I)

with a trans-2-(leaving group substituted) methyl-3-akylacrylic acid of the formula

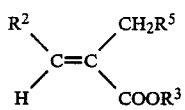 (III)

and a reducing metal having an oxido-reduction potential of −0.1 to −0.8 volt, wherein $R^1$ is hydrogen, 1C to 10C alkyl, 1C to 10C haloalkyl, 4C to 8C dioxolenyl, or 1C to 10C hydroxyalkyl in which the hydroxy group is unprotected or is protected by a hydroxy protecting group, $R^2$ is 1C to 8C alkyl or 1C to 8C substituted by a member selected from the group consisting of halogen, cyano, carbamoyl, carboxy, protected carboxy, alkenyl, alkinyl, amino, ureido, formimidoyl, hydroxy, protected hydroxy, alkanoyloxy, carbamoyloxy, hydroxyalkyloxy, aminoalkoxy, haloalkoxy, alkylthio, aminoalkylthio, hydroxyalkylthio, protected hydroxyalkylthio, haloalkylthio, alkylsulfinyl, aminoalkylsulfinyl, hydroxyalkylsulfinyl, protected hydroxyalkylsulfinyl, haloalkylsulfinyl, alkylsulfonyl, aminoalkylsulfonyl, hydroxyalkylsulfonyl, protected hydroxyalkylsulfonyl and haloalkylsulfonyl, $R^3$ is hydrogen or a carboxy protecting group, and $R^4$ and $R^5$ each is hydroxy, halogen, 1C to 8C alkanoyloxy which is unsubstituted or is further substituted, 7C to 15C aroyloxy, 1C to 8C alkylsulfonyloxy, 6C to 10C arylsulfonyloxy, 1C to 8C alkylsulfinyl, or 6C to 10C arylsulfinyl.

2. A process as claimed in claim 1 wherein $R^1$ is 1C to 10C alkyl, 1C to 10C hydroxyalkyl which is unprotected or protected by 3C to 18C hydrocarbylsilyl, 1C to 8C haloalkyl, or 4C to 8C dioxolenyl.

3. A process as claimed in claim 1 wherein $R^1$ is hydrogen, 1C to 8C alkyl, or 1C to 8C 1-(hydroxy, protected hydroxy or halo)alkyl.

4. A process as claimed in claim 3 wherein the optional protective group is 1C to 10C carboxylic acyl, 2C to 10C carbonic acyl, 2C to 8C ether forming group, 3C to 18C trihydrocarbylsilyl, or 7C to 19C reactive aralkyl.

5. A process as claimed in claim 1 wherein $R^1$ is 1-hydroxyethyl, 1-tert-butyldimethylsilyloxy)ethyl, or 1-(triethylsilyloxy)ethyl.

6. A process as claimed in claim 1 wherein $R^2$ is 1C to 3C alkyl or 1C to 5C haloalkyl.

7. A process as claimed in claim 1 wherein $R^2$ is methyl or ethyl.

8. A process as claimed in claim 1 wherein $R^3$ is hydrogen or 1C to 8C alkyl.

9. A process as claimed in claim 1 wherein $R^3$ is hydrogen, methyl or ethyl.

10. A process as claimed in claim 1 wherein $R^4$ and $R^5$ each is fluorine, chlorine, bromine, 1C to 8C alkanoyloxy, 7C to 15C aroyloxy, 1C to 8C alkylsulfonyloxy, 1C to 8C substituted alkylsulfonyloxy, 6C to 10C arylsulfonyloxy, 1C to 8C alkylsulfinyl, or 6C to 10C arylsulfinyl.

11. A process as claimed in claim 10 wherein $R^4$ is acetoxy and $R^5$ is bromine.

12. A process as claimed in claim 1 wherein the reaction is carried out in a solvent.

13. A process as claimed in claim 12 wherein the solvent is tetrahydrofuran.

14. A process as claimed in claim 1 wherein the reducing metal is zinc.

15. A process as claimed in claim 14 wherein zinc is activated with cupric bromide.

16. A process as claimed in claim 1 wherein the reaction is carried out at −10° to 50° C. for 0.5 to 10 hours.

17. A process as claimed in claim 16 wherein the reaction is carried out at 30° to 35° C. for 3.5 hours.

* * * * *